United States Patent
Thallapuranam et al.

(10) Patent No.: US 10,385,113 B2
(45) Date of Patent: Aug. 20, 2019

(54) ENGINEERED FGF COMPOSITIONS AND METHODS OF USE THEREOF

(71) Applicant: THE BOARD OF TRUSTEES OF THE UNIVERSITY OF ARKANSAS, Little Rock, AR (US)

(72) Inventors: Suresh Kumar Thallapuranam, Fayetteville, AR (US); David A. Zaharoff, Morrisville, NC (US); Srinivas Jayanthi, Fayetteville, AR (US); Bhanuprasanth Koppolu, Cary, NC (US); Rebecca Kerr, Fayetteville, AR (US); Kartik Balachandran, Fayetteville, AR (US); David S. McNabb, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 15/474,268

(22) Filed: Mar. 30, 2017

(65) Prior Publication Data
US 2017/0281790 A1  Oct. 5, 2017

Related U.S. Application Data

(60) Provisional application No. 62/315,233, filed on Mar. 30, 2016.

(51) Int. Cl.
| | |
|---|---|
| *A61K 38/18* | (2006.01) |
| *A61K 38/00* | (2006.01) |
| *A61K 38/16* | (2006.01) |
| *A61K 47/68* | (2017.01) |
| *C07K 14/50* | (2006.01) |
| *C07K 14/71* | (2006.01) |

(52) U.S. Cl.
CPC .............. *C07K 14/71* (2013.01); *A61K 38/16* (2013.01); *A61K 47/68* (2017.08); *C07K 14/50* (2013.01); *A61K 38/00* (2013.01); *A61K 38/1825* (2013.01); *C07K 14/501* (2013.01); *C07K 14/503* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,982,170 B1 | 1/2006 | Maciag | |
| 7,790,682 B1 * | 9/2010 | Blaber | C07K 14/501 435/320.1 |
| 8,153,770 B1 | 4/2012 | Blaber | |
| 9,464,126 B2 * | 10/2016 | Mohammadi | C07K 14/50 |
| 9,926,355 B2 * | 3/2018 | Mohammadi | C07K 14/50 |
| 2006/0217310 A1 | 9/2006 | Chiu et al. | |
| 2010/0286042 A1 | 11/2010 | Imamura et al. | |
| 2015/0111821 A1 | 4/2015 | Suh et al. | |
| 2016/0237133 A1 * | 8/2016 | Suh | A61K 38/1825 |

FOREIGN PATENT DOCUMENTS

| | | |
|---|---|---|
| CN | 103169658 | 6/2013 |
| CN | 103396985 | 11/2013 |
| CN | 104162148 | 11/2014 |
| WO | WO 1995/026737 | 10/1995 |
| WO | WO 2006/073417 | 7/2006 |
| WO | WO 2009/020802 | 2/2009 |
| WO | WO 2013068776 | 5/2013 |
| WO | WO 2014084027 | 6/2014 |
| WO | WO 2014130659 | 8/2014 |
| WO | WO 2015121457 | 12/2016 |

OTHER PUBLICATIONS

Pellegrini et al., Nature, 407:1029-1034, 2000.*
DiGabriele et al., Nature, 395:812-817, 1998.*
Schlessinger et al., Molecular Cell, 6:743-750, 2000.*
Thompson et al., Biochemistry, 33:3831-40, 1994.*
Andreopoulos, F.M. & Persaud, I. Delivery of basic fibroblast growth factor (bFGF) from photoresponsive hydrogel scaffolds. Biomaterials 27, 2468-2476 (2006).
Arunkumar, A.I. et al. Oligomerization of acidic fibroblast growth factor is not a prerequisite for its cell proliferation activity. Protein Sci 11, 1050-1061 (2002).
Arunkumar, A.I. et al. Structure and stability of an acidic fibroblast growth factor from Notophthalmus viridescens. J Biol Chem 277, 46424-46432 (2002).
Asai, J. et al. Topical application of ex vivo expanded endothelial progenitor cells promotes vascularisation and wound healing in diabetic mice. Int Wound J 10, 527-533 (2012).
Bernett, M.J., Somasundaram, T. & Blaber, M. An atomic resolution structure for human fibroblast growth factor 1. Proteins 57, 626-634 (2004).
Brewster, L.P. et al. Construction and characterization of a thrombin-resistant designer FGF-based collagen binding domain angiogen. Biomaterials 29, 327-336 (2008).

(Continued)

*Primary Examiner* — Marianne P Allen
(74) *Attorney, Agent, or Firm* — Quarles & Brady LLP

(57) ABSTRACT

The present invention relates to the development of stable mutants of FGF-1 and FGF-2. In particular, it relates to novel engineered FGF-1 and FGF-2 polypeptides as well as polynucleotides, DNA constructs, and vectors encoding such polypeptides. In another aspect, pharmaceutical compositions and hydrogels including the disclosed polypeptides, polynucleotides, DNA constructs, and vectors are provided. In a still further aspect, methods of treating conditions using the compositions disclosed herein are provided.

20 Claims, 22 Drawing Sheets
(17 of 22 Drawing Sheet(s) Filed in Color)
Specification includes a Sequence Listing.

(56) References Cited

OTHER PUBLICATIONS

Cai, S., Liu, Y., Zheng Shu, X. & Prestwich, G.D. Injectable glycosaminoglycan hydrogels for controlled release of human basic fibroblast growth factor. Biomaterials 26, 6054-6067 (2005).
Comerota, A. J. et al. Naked plasmid DNA encoding fibroblast growth factor type 1 for the treatment of end-stage unreconstructible lower extremity ischemia: preliminary results of a phase I trial. J. Vasc. Surg. 35,930-936 (2002).
Culajay, J.F., Blaber, S.I., Khurana, A. & Blaber, M. Thermodynamic characterization of mutants of human fibroblast growth factor 1 with an increased physiological half-life. Biochemistry 39, 7153-7158 (2000).
Dubey, V.K., Lee, J. & Blaber, M. Redesigning symmetry-related "mini-core" regions of FGF-1 to increase primary structure symmetry: thermodynamic and functional consequences of structural symmetry. Protein Sci 14, 2315-2323 (2005).
Erzurum, V.Z. et al. R136K fibroblast growth factor-1 mutant induces heparin-independent migration of endothelial cells through fibrin glue. J Vasc Surg 37, 1075-1081 (2003).
Hung, K.W. et al. Solution structure of the ligand binding domain of the fibroblast growth factor receptor: role of heparin in the activation of the receptor. Biochemistry 44, 15787-15798 (2005).
Kelpke, S.S., Zinn, K.R., Rue, L.W. & Thompson, J.A. Site-specific delivery of acidic fibroblast growth factor stimulates angiogenic and osteogenic responses in vivo. J Biomed Mater Res A 71, 316-325 (2004).
Khanna, O., J. C. Larson, et al. "Generation of alginate microspheres for biomedical applications." J Vis Exp(66), 2012.
Lin, P. H., Cheng, H., Huang, W. C. & Chuang, T. Y. Spinal cord implantation with acidic fibroblast growth factor as a treatment for root avulsion in obstetric brachial plexus palsy. J. Chin. Med. Assoc. 68,392-396 (2015).
Lin, W. H., L. J. Xiang, et al. "Fibroblast growth factors stimulate hair growth through beta-catenin and Shh expression in C57BL/6 mice." Biomed Res Int 2015: 730139.
Martin, P. Wound healing—aiming for perfect skin regeneration. Science 276, 75-81 (1997).
Motomura, K. et al. An FGF1:FGF2 chimeric growth factor exhibits universal FGF receptor specificity, enhanced stability and augmented activity useful for epithelial proliferation and radioprotection. Biochim Biophys Acta 1780, 1432-1440 (2008).
Moya, M.L. et al. The effect of FGF-1 loaded alginate microbeads on neovascularization and adipogenesis in a vascular pedicle model of adipose tissue engineering. Biomaterials 31, 2816-2826 (2010).
Nikol, S. et al. Therapeutic angiogenesis with intramuscular NV1FGF improves amputation-free survival in patients with critical limb ischemia. Mol. Ther. 16, 972-978 (2008).
Shireman, P.K., Xue, L., Maddox, E., Burgess, W.H. & Greisler, H.P. The S130K fibroblast growth factor-1 mutant induces heparin-independent proliferation and is resistant to thrombin degradation in fibrin glue. J Vasc Surg 31, 382-390 (2000).
Shoichet, B.K., Baase, W.A., Kuroki, R. & Matthews, B.W. A relationship between protein stability and protein function. Proc Natl Acad Sci U S A 92, 452-456 (1995).
Sokic, S. and G. Papavasiliou "FGF-1 and proteolytically mediated cleavage site presentation influence three-dimensional fibroblast invasion in biomimetic PEGDA hydrogels." Acta Biomater 8(6): 2213-22, 2012.
Szlachcic, A. et al. Structure of a highly stable mutant of human fibroblast growth factor 1. Acta Crystallogr D Biol Crystallogr 65, 67-73 (2009).
Takahashi, M. et al. Fibroblast growth factor-1-induced ERK1/2 signaling reciprocally regulates proliferation and smooth muscle cell differentiation of ligament-derived endothelial progenitor cell-like cells. Int J Mol Med 29, 357-364 (2012).
Tassi, E. et al. Enhancement of fibroblast growth factor (FGF) activity by an FGF-binding protein. J Biol Chem 276, 40247-40253 (2001).
Tsai, E.C., Dalton, P.D., Shoichet, M.S. & Tator, C.H. Matrix inclusion within synthetic hydrogel guidance channels improves specific supraspinal and local axonal regeneration after complete spinal cord transection. Biomaterials 27, 519-533 (2006).
Tsai, M. J., S. K. Tsai, et al. "Acidic FGF promotes neurite outgrowth of cortical neurons and improves neuroprotective effect in a cerebral ischemic rat model." Neuroscience 305: 238-47, 2015.
Tunyogi-Csapo, M. et al. Role of fibroblasts and fibroblast-derived growth factors in periprosthetic angiogenesis. J Orthop Res 25, 1378-1388 (2007).
Wang, Y., H. Lin, et al. "Cell-penetrating peptide TAT-mediated delivery of acidic FGF to retina and protection against ischemia-reperfusion injury in rats." J Cell Mol Med 14(7): 1998-2005 2010.
Xia, X., J. P. Babcock, et al. "Pharmacokinetic properties of 2nd-generation fibroblast growth factor-1 mutants for therapeutic application." PLoS One 7(11): e48210, 2012.
Xue, L., Shireman, P.K., Hampton, B., Burgess, W.H. & Greisler, H.P. The cysteine-free fibroblast growth factor 1 mutant induces heparin-independent proliferation of endothelial cells and smooth muscle cells. J Surg Res 92, 255-260 (2000).
Yeh, B.K. et al. Structural basis for activation of fibroblast growth factor signaling by sucrose octasulfate. Mol Cell Biol 22, 7184-7192 (2002).
Zakrzewska, M., Marcinkowska, E. & Wiedlocha, A. FGF-1: from biology through engineering to potential medical applications. Crit Rev Clin Lab Sci 45, 91-135 (2008).
Zhang, J. and Y. Li "Therapeutic uses of FGFs." Semin Cell Dev Biol. 2016.
Zheng, L., Q. Hui, et al. "TAT-Mediated Acidic Fibroblast Growth Factor Delivery to the Dermis Improves Wound Healing of Deep Skin Tissue in Rat." PLoS One 10(8): e013529. 2015.
Kobielak, A. et al., "Protease resistant variants of FGF1 with prolonged biological activity." Protein Pept Lett 21(5): 434-443 (2014).

* cited by examiner

Figure 1

Nucleic Acid Sequence of wtFGF-1 (SEQ ID NO: 1):
DNA sequence (coding from AA 15-155)

5'-atg ttt aat ctg cct cca ggg aat tac aag aag ccc aaa ctc ctc tac tgt agc aac ggg ggc cac ttc
ctg agg atc ctt ccg gat ggc aca gtg gat ggg aca gtg gat ggg aca gtg gac agg agg gac aca cac att cag ctg cag
ctc agt gcg gaa agc gtg ggg gag gtg tat ata aag agt acc gag act ggc cag tac ttg gcc atg gac
acc gac ggg ctt tta tac ggc tca cag aca cca aat gag gaa tgt ttg ttc ctg gaa agg ctg gag
aac cat tac aac acc tat ata tcc aag aag cat gca gag aag aat tgg ttt gtt ggc ctc aag aag aat
ggg agc tgc aaa cgc ggt cct cgg act cac tat ggc cag aaa gca atc ttg ctc ccc ctg cca gtc
tct tct gat taa-3'

Amino acid sequence of wtFGF-1(140) (SEQ ID NO: 2)

FNLPPGNYKKPKLLYCSNGGHFLRILPDGTVDGTRDRSDQHIQLQLSAESVGEV
YIKSTETGQYLAMDTDGLLYGSQTPNEECLFLERLEENHYNTYISKKHAEKNW
FVGLKKNGSCKRGPRTHYGQKAILFLPLPVSSD

Figure 2

Nucleic Acid Sequence of FGF-1R136E (SEQ ID NO: 3):
DNA sequence (coding from AA 15-155)
5'-atg ttt aat ctg cct cca ggg aat tac aag ccc aaa ctc ctc tac tgt agc aac ggg ggc cac ttc
ctg agg atc ctt ccg gat ggc aca gtg gat ggg aca gtg gat ggg agc gac cag cac att cag ctg cag
ctc agt gcg aag agc gtg ggg gag gtg tat ata aag agt act ggc cag tac ttg gcc atg gac
acc gac ctt tta tac ggc tca cag aca cca aat gag gaa tgt ttg ttc ctg gaa agg ctg gag gag
aac cat tac aac acc tat ata tcc aag aag cat gca gag aag aat tgg ttt gtt ggc ctc aag aag aat
ggg agc tgc aaa cgc ggt cct gag act cac tat ggc cag aaa gca atc ttg ttt ctc ccc ctg cca gtc
tct tct gat taa-3'

Amino acid sequence of FGF-1R136E (140) (SEQ ID NO: 4)

FNLPPGNYKPKLLYCSNGGHFLRILPDGTVDGTRDRSDQHIQLQLSAESVGEV
YIKSTETGQYLAMDTDGLLYGSQTPNEECLFLERLEENHYNTYISKKHAEKNW
FVGLKKNGSCKRGPETHYGQKAILFLPLPVSSD

Figure 3

Nucleic Acid Sequence of FGF-1R136D (SEQ ID NO: 5):
DNA sequence (coding from AA 15-155)
5'-atg ttt aat ctg cct cca ggg aat tac aag aag ccc aaa ctc ctc tac tgt agc aac ggg ggc cac ttc
ctg agg atc ctt ccg gat ggc aca gtg gat ggg aca agg gac agg gac agc cag cac att cag ctg cag
ctc agt gcg gaa agc gtg ggg gag gtg tat ata aag agt acc gag act ggc cag tac ttg gcc atg gac
acc gac ggg ctt tta tac ggc tca cag aca cca aat gag gaa tgt ttg ttc ctg gaa agg ctg gag gag
aac cat tac aac acc tat ata tcc aag aag cat gca gag aag aat tgg ttt gtt ggc ctc aag aag aat
ggg agc tgc aaa cgc ggt cct gat act cac tac ggc cag aaa gca atc ttg ttt ctc ccc ctg cca gtc
tct tct gat taa-3'

Amino acid sequence of FGF-1R136D (140) (SEQ ID NO: 6)

FNLPPGNYKKPKLLYCSNGGHFLRILPDGTVDGTRDRSDQHIQLQLSAESVGEV
YIKSTETGQYLAMDTDGLLYGSQTPNEECLFLERLEENHYNTYISKKHAEKNW
FVGLKKNGSCKRGPDTHYGQKAILFLPLPVSSD

Figure 4
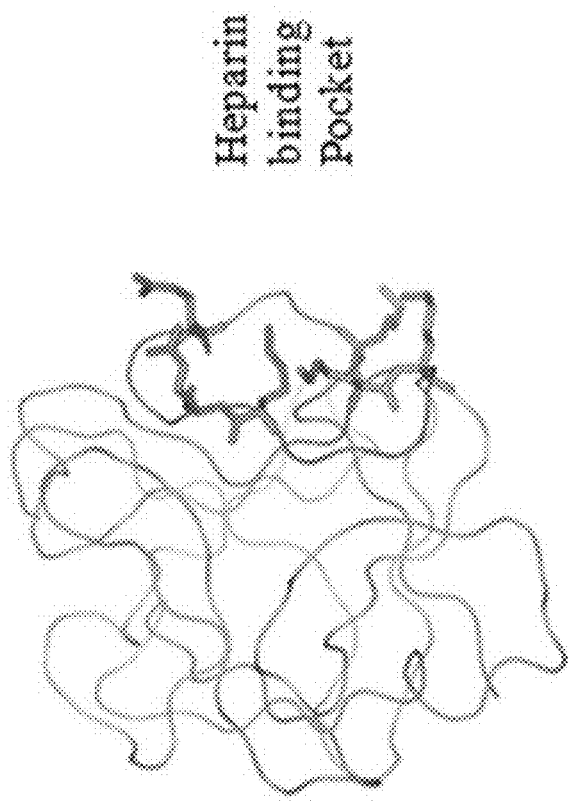
Fig. 4B
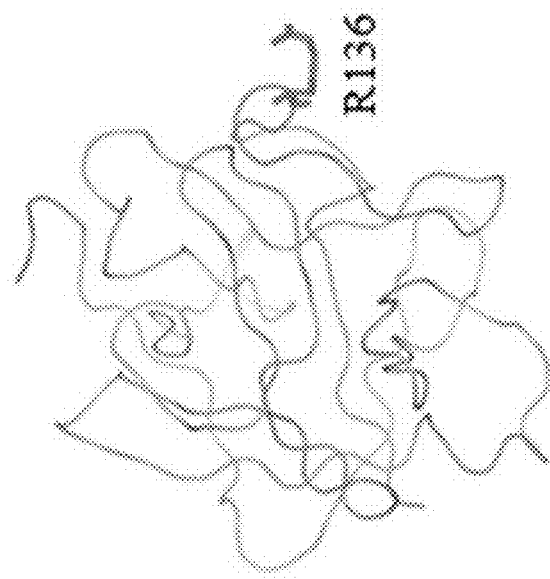
Fig. 4A

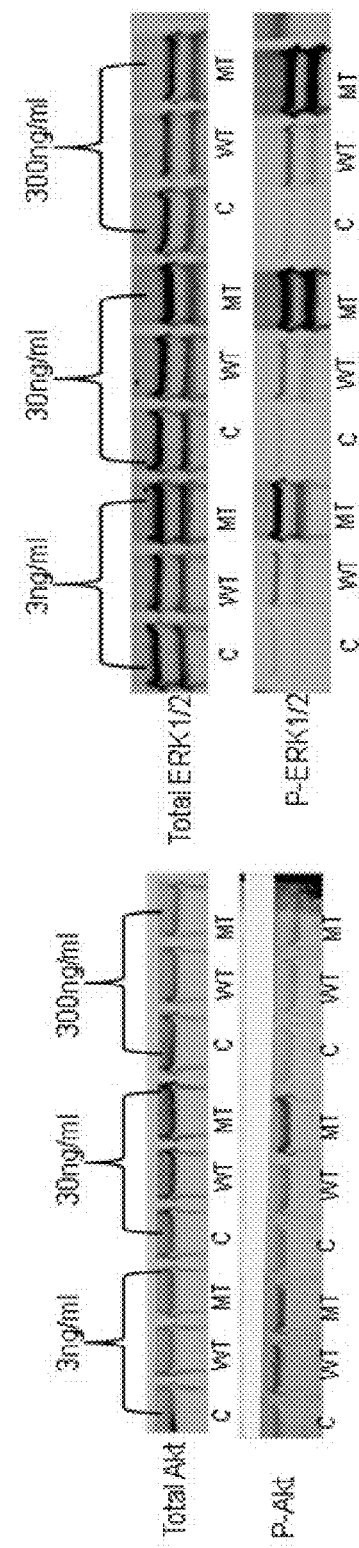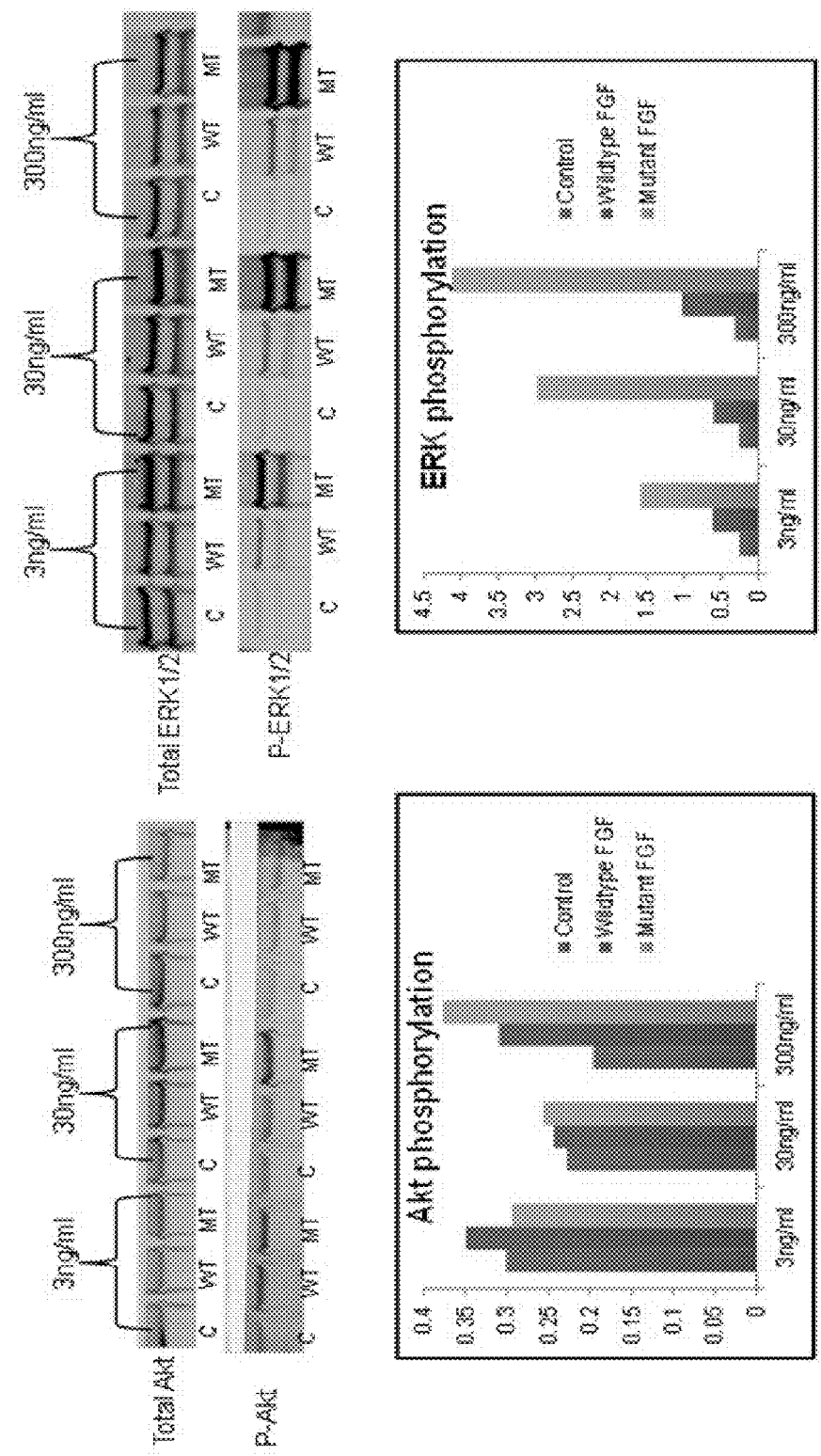
Fig. 11A
Fig. 11B

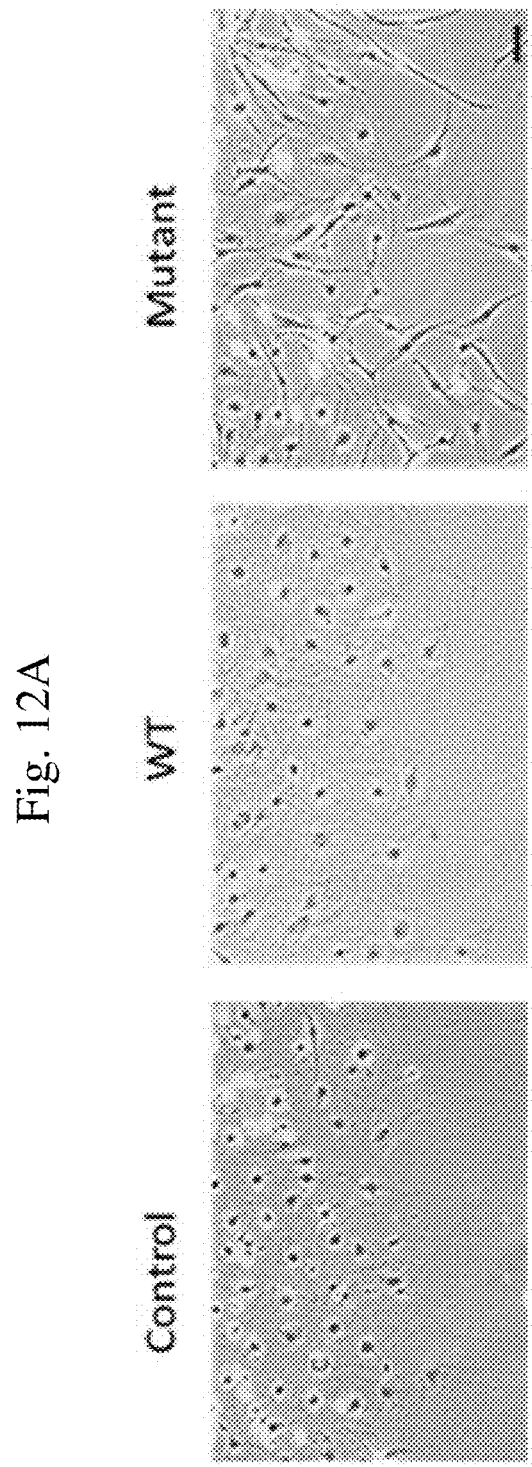

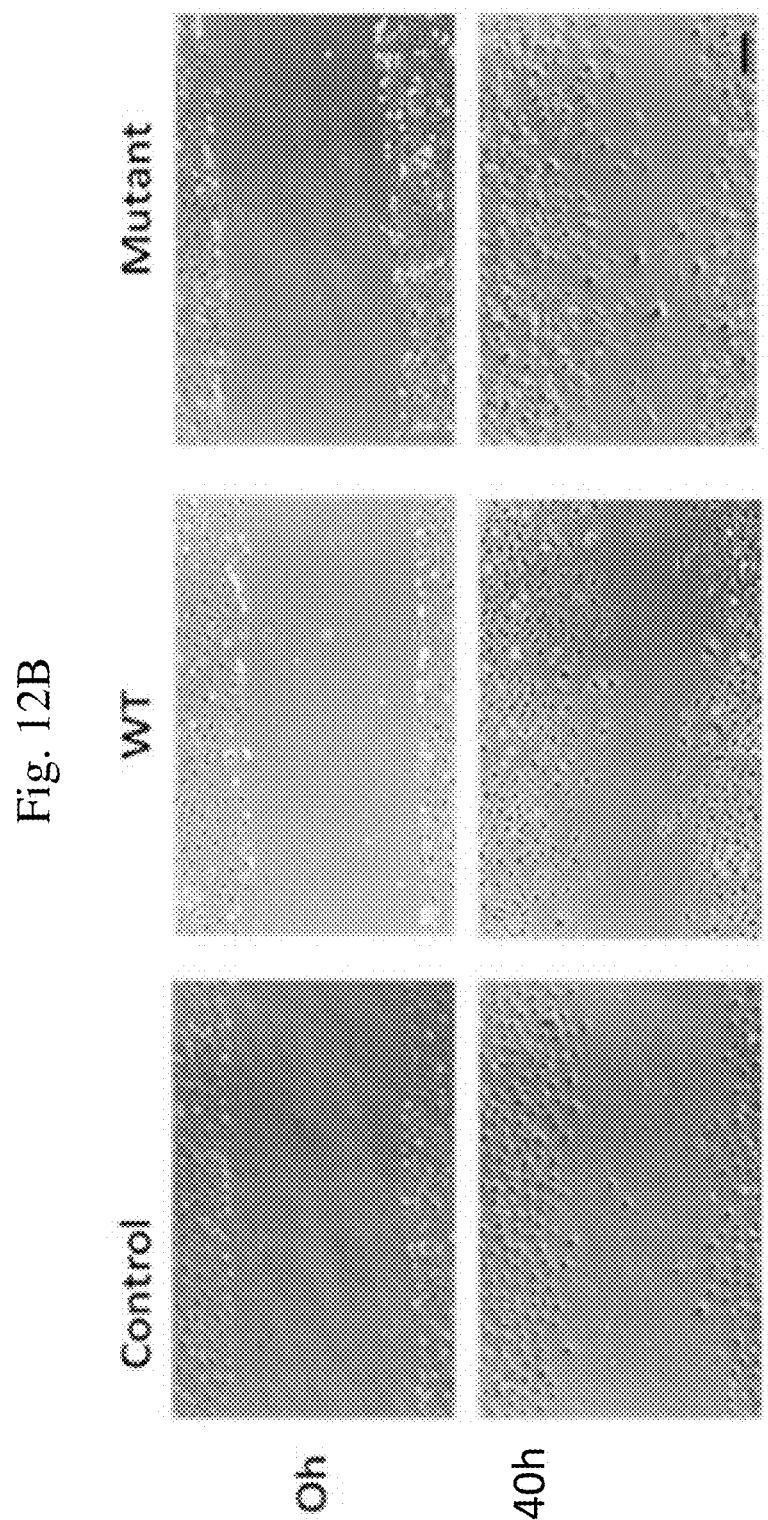

Figure 13

Nucleic Acid Sequence of wtFGF-2 (SEQ ID NO: 7):

ATGGCAGCCGGGAGCATCACCACGCTGCCTGCCCTTGCCCTGAGGATGGCGG
CAGCGGGCGCCTTCCCGCCGGGCCACTTCAAGGACCCCAAGCGGCTGTACT
GCAAAAACGGGGGCTTCTTCCTGCGCATCCACCCGGACGGCGAGTTGAC
GGGGTCCGGAGAAGAGGGAGTTGTCTATCAAGGAGTGTGTAACCGTACCTGGC
AGAGAGAGGAGTTGTCTATCAAGGAGTGTGTAACCGTACCTGGC
TATGAAGGAAGATGGAAGATTACTGGCTTCTAAATGTACGATGAGTGT
TTCTTTTTGAACGATTGGAATCTAATAACTACAATACTACCGGTCAAGGAA
ATACACCAGTTGGTATGTGGCACTGAAACGAACTGGGCAGTATAAACTTGGA
TCCAAAACAGGACCTGGGCAGAAAGCTATACTTTTCTTCCAATGTCTGCTAA
GAGCTAG

Amino acid sequence of wtFGF-2 with the K138 site (SEQ ID NO: 8):

MAAGSITTLPALPEDGGSGAFPPGHFKDPKRLYCKNGGFFLRIHPDGRVDGVRE
KSDPHIKLQLQAEERGVVSIKGVCANRYLAMKEDGRLLASKCVTDECFFFERLES
NNYNTYRSRKYTSWYVALKRTGQYKLGSKTGPGQKAILFLPMSAKS*

Figure 14

Nucleic Acid Sequence of FGF-2K138E (SEQ ID NO: 9):
ATGGCAGCGGGAGCGGAGCATCACCACGCGCCTGCCCGCCTTGCCCGAGGATGGCGG
CAGCGGCGCCTTCCCGCCGGGCCACTTCAAGGACCCCAAGCGGCTGTACT
GCAAAAACGGGGGCTTCTTCCTGCGCATCCACCCGACGGCCGAGTTGAC
GGGGTCCGGAGAAGAGGAGTTGTGTCTATCAAGGAGTGTGTAACTTAAGCAGA
AGAGAGGAGGAGTTGTGTCTATCAAGGAGTGTGTAACCGTTACCTGGC
TATGAAGGAAGATGGAAGATTACTGGCTTCTAAATGTGTACGATGAGTGT
TTCTTTTGAACGATTGGAATCTAATAACTACAATACTTACCGGTCAAGGAA
ATACACCAGTTGGTATGTGGCACTGAAACGAATGGGCAGTATAAACTTGGA
TCCGAAACAGGACCTGGGCAGAAAAGTATACTTTCTTCCAATGTCTGCTAA
GAGCTAG Amino acid sequence of FGF-2K138E (SEQ ID NO: 10):
MAAGSITTLPALPEDGGSGAFPPGHFKDPKRLYCKNGGFFLRIHPDGRVDGVRE
KSDPHIKLQLQAEERGVVSIKGVCANRYLAMKEDGRLLASKCVTDECFFFERLES
NNYNTYRSRKYTSWYVALKRTGQYKLGSETGPGQKAILFLPMSAKS*

Figure 15

Nucleic Acid Sequence of FGF-2K138D (SEQ ID NO: 11):
ATGGCAGCCGGGAGCATCACCACGCTGCCCGCTTGCCCGAGGATGGCGG
CAGCGGGGCCTTCCCGCCGGGCCACTTCAAGGACCCCAAGCGGCTGTACT
GCAAAAACGGGGGCTTCTTCCTGCGCATCCACCCCGACGGCCGAGTTGAC
GGGGTCCGGGAGAAGAGCGACCCTCACATCAAGCTACAACTTCAAGCAGA
AGAGAGAGGAGTTGTGTCTATCAAAGGAGTGTGTGCTAACCGTTACCTGGC
TATGAAGGAAGATGGAAGATTACTGGCTTCTAAATGTGTTACGGATGAGTGT
TTCTTTTTTGAACGATTGGAATCTAATAACTACAATACTTACCGGTCAAGGAA
ATACCAGTTGGTATGTGGCACTGAAAACGAACTGGGCAGTATAAACTTGGA
TCCGACACAGGACCCTGGGCAGAAAGCTATACTTTTCTTCCAATGTCTGCTAA
GAGCTAG Amino acid sequence of FGF-2K138D (SEQ ID NO: 12):
MAAGSITTLPALPEDGGSGAFPPGHFKDPKRLYCKNGGFFLRIHPDGRVDGVRE
KSDPHIKLQLQAEERGVVSIKGVCANRYLAMKEDGRLLASKCVTDECFFFERLES
NNYNTYRSRKYTSWYVALKRTGQYKLGSDTGPGQKAILFLPMSAKS*

ENGINEERED FGF COMPOSITIONS AND METHODS OF USE THEREOF

CROSS-REFERENCE TO RELATED PATENT APPLICATIONS

The present application claims the benefit of priority of U.S. Provisional Patent Application No. 62/315,233, filed Mar. 30, 2016, the content of which is incorporated herein by reference in its entirety.

STATEMENT REGARDING FEDERALLY SPONSORED RESEARCH

This invention was made with government support under grant numbers NCRR COBRE Grant 1 P20 RR15569 and P30 GM103450 awarded by the National Institutes of Health, Grant DE-FG02-01ER15161 awarded by the Department of Energy, and Grant IOS0843397 9TO awarded by the National Science Foundation. The United States Government has certain rights in the invention.

SEQUENCE LISTING

A Sequence Listing accompanies this application and is electronically submitted in .txt format. The .txt file contains a sequence listing entitled "2017-06-19 5965-00079 ST25.txt ." The Sequence Listing contained in this .txt file is part of the specification and is hereby incorporated by reference herein in its entirety.

INTRODUCTION

The present invention relates to the development of stable mutants of FGF-1 and FGF-2. It relates in particular to polynucleotides, polypeptides, and pharmaceutical compositions including such mutant forms of FGF-1 and FGF-2 as well as methods of treating conditions using such compositions.

FGFs play an important role in various cellular processes like cell proliferation, migration, differentiation and induce processes such as regeneration, morphogenesis and angiogenesis. FGFs exert their effects upon binding to their specific receptors. These molecules are known to bind to heparin to increase the efficiency of mitogenic activity.

Growth factors like FGF-1 and FGF-2 also have a huge clinical significance. FGF-1 is known to play a crucial role in wound healing and other significant clinical conditions. For example, there are reports demonstrating the FGF-1 has significant nerve regeneration and potent angiogenic activity. These events are critical for proper healing after an injury. Hence administration of FGF-1 during an injury can quicken the process of healing and helps in safe recovery from trauma. Although FGF-1 and FGF-2 proteins are promising therapeutics, they are highly susceptible to proteolytic degradation especially by thrombin which is usually present in abundance at the site of a wound in the fibrin clots. Thus, there is a need in the art for new FGF-based treatments having increased stability against proteolytic degradation, higher biological activity, and a prolonged circulation half-life.

SUMMARY

The present invention relates to the development of stable mutants of FGF-1 and FGF-2. In one aspect, FGF polypeptides are provided. The FGF polypeptides may include SEQ ID NO: 4, SEQ ID NO: 6, a polypeptide having 80% sequence identity to amino acids 1-121; 123-140 of SEQ ID NO: 4, a polypeptide having 80% sequence identity to amino acids 1-121; 123-140 of SEQ ID NO: 6, SEQ ID NO: 10, SEQ ID NO: 12, a polypeptide having 80% sequence identity to amino acids 1-137; 139-155 of SEQ ID NO: 10, a polypeptide having 80% sequence identity to amino acids 1-137; 139-155 of SEQ ID NO: 12, fragments including amino acid residue 122 of SEQ ID NO: 4 or SEQ ID NO: 6, fragments including amino acid residue 138 of SEQ ID NO: 10 or SEQ ID NO: 12, a polypeptide having 80% sequence identity to at least one of SEQ ID NOs: 4, 6, 10 or 12, fragments comprising amino acid residue 122 of SEQ ID NO: 4 or SEQ ID NO: 6, fragments comprising amino acid residue 138 of SEQ ID NO: 10 or SEQ ID NO: 12, a fragment of SEQ ID NOs: 4 or 6 comprising amino acids 112-128 and a fragment of SEQ ID NOs: 10 or 12 comprising amino acids 128-144.

In another aspect, polynucleotides encoding any one of the FGF polypeptides described herein are provided.

In a further aspect, provided herein are pharmaceutical compositions including any one of the FGF polypeptides or polynucleotides described herein.

In another aspect, methods of treating a condition are provided. The methods may include administering any one of the compositions (FGF polypeptides, FGF polynucleotides, or pharmaceutical compositions) described herein to a subject in an amount effective to treat the condition.

In still further aspects, the compositions may be included in a hydrogel or may be encoded by a construct and/or produced as a fusion protein with a membrane permeable protein.

BRIEF DESCRIPTION OF THE DRAWINGS

This patent or application contains at least one drawing executed in color. Copies of this patent or patent application publication with color drawings will be provided by the Office upon request and the payment of the necessary fee.

FIG. 1 shows the nucleotide sequence of the wild type (wt) FGF-1 molecule (SEQ ID NO: 1) with a codon for arginine at position 136 underlined. Also represented is the translated amino acid sequence of the wtFGF-1 (SEQ ID NO: 2) with the residue R136 underlined. As shown with SEQ ID NO: 2, the recombinant clone used in the Examples is devoid of the first 14 amino acids present at the N-terminus. Truncated FGF-1 showed no difference in biological activity compared to the full length form and is generally used and accepted in the field.

FIG. 2 shows the nucleotide sequence of FGF-1R136E molecule (SEQ ID NO: 3) with a codon for glutamic acid at position 136 underlined. Also represented is the translated amino acid sequence of the FGF-1R136E polypeptide (SEQ ID NO: 4) with the R136E substitution underlined. The R136E substitution is at position 122 in the sequence shown.

FIG. 3 shows the nucleotide sequence of FGF-1R136D molecule (SEQ ID NO: 5) with a codon for aspartic acid at position 136 of the full-length sequence underlined. Also represented is the translated amino acid sequence of the FGF-1R136D polypeptide (SEQ ID NO: 6) with the R136E substitution underlined. As noted above, the R136D substitution is at position 122 in the sequence shown.

FIG. 4 shows the 3D structure of the FGF-1 molecule using a ribbon diagram. Amino acid residue R136 that is very important in the function of the FGF-1 mitogenic activity is highlighted and represented in stick form (FIG. 4A). In the picture shown in FIG. 4B, the amino acid residues that play an important role in the heparin binding are highlighted. All these amino acid residues are shown in sticks and colored in orange.

Figure 5:
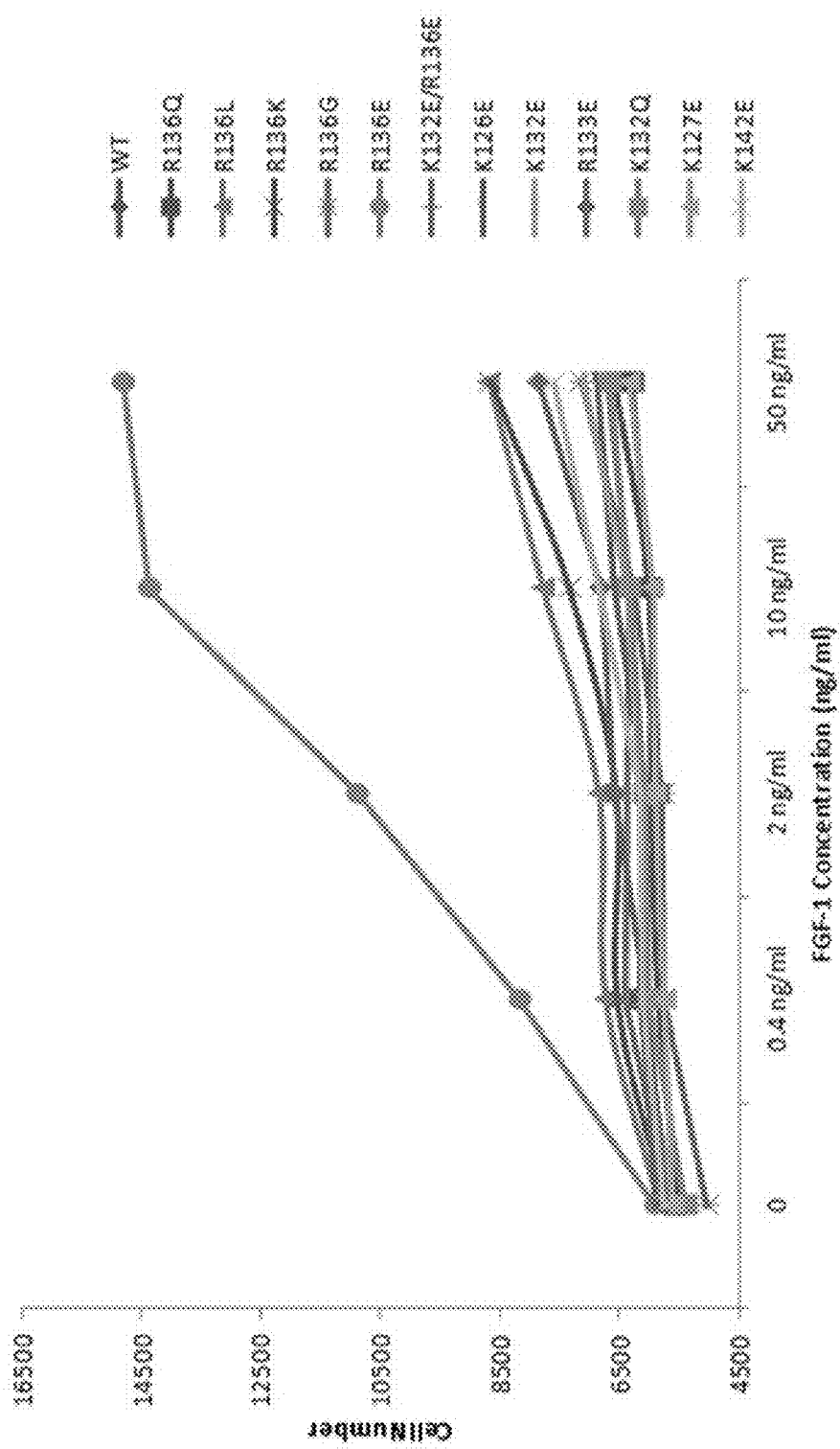
FIG. 5 shows a graph of a mitogenic activity assay of the wild type and mutant forms FGF-1, where the mutant FGF-1 R136E shows approximately 2 fold increased mitogenic activity compared to the wtFGF-1 and other mutant forms of FGF-1. This signifies that charge reversal especially using glutamic acid in place of arginine at position 136 might actually be enhancing the overall stability of the FGF-1 molecule.

The DNA sequence of the "wild-type" FGF-1 protein from humans is presented as SEQ ID NO:1 while the amino acid sequence of residues 15-155 is depicted as SEQ ID NO: 2. See FIG. 1. The DNA sequence of the "wild-type" FGF-2 protein from humans is presented as SEQ ID NO: 7 while the amino acid sequence of residues 1-155 is depicted as SEQ ID NO: 8. See FIG. 13.

Amino acid sequences for the engineered mutant FGF polypeptides disclosed herein are provided as SEQ ID NO: 4 (FGF-1R136E), SEQ ID NO: 6 (FGF-1R136D), SEQ ID NO: 10 (FGF-2K138E), and SEQ ID NO: 12 (FGF-2K138D). These sequences may be used as reference sequences.

The FGF polypeptides provided herein may be full-length polypeptides (i.e., SEQ ID NOS: 4, 6, 10, or 12) or may be fragments of the full-length FGF polypeptide including amino acid residue 122 of SEQ ID NO: 4 or SEQ ID NO: 6 or amino acid residue 138 of SEQ ID NO: 10 or SEQ ID NO: 12.

As used herein, a "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 155 contiguous amino acid residues of a reference polypeptide, respectively. In some embodiments, a fragment may comprise at least 5, 10, 15, 20, 25, 30, 40, 50, 60, 70, 80, 90, 100, or 150 contiguous amino acid residues of a reference polypeptide. Fragments may be preferentially selected from certain regions of a molecule. The term "at least a fragment" encompasses the full length polypeptide. A fragment of a FGF-1 polypeptide may comprise or consist essentially of a contiguous portion of an amino acid sequence of the full-length FGF polypeptide (SEQ ID NOS: 4, 6, 10, or 12). A fragment may include an N-terminal truncation, a C-terminal truncation, or both truncations relative to the full-length FGF polypeptide.

Preferably, a fragment of a FGF-1 polypeptide includes amino acid residue 122 of SEQ ID NO: 4 or SEQ ID NO: 6. Preferably, a fragment of a FGF-2 polypeptide includes amino acid residue 138 SEQ ID NO: 10 or SEQ ID NO: 12. Suitable fragments include or consist of amino acid residues 112-128, 106-134, 100-140, 50-140, 25-140, 10-140, 2-140 or any range therein of SEQ ID NOs: 4 or 6, or amino acid residues 128-144, 120-150, 110-155, 100-155, 80-155, 60-155, 40-155, 20-155, 10-155, 2-155 or any range therein of SEQ ID NOs: 10 or 12.

FGF polypeptides may be useful for a variety of reasons. For example, FGF polypeptides which contain the substitutions noted above can be used inter alia for raising antibodies. Such polypeptides are typically less than full-length proteins. Preferably such residues are at least 6, 7, 8, 9, 10, 11, 12, 13, 14, 15, 17, 19, 21, 23, 25, 30, 40, 50 or more residues in length. As an example, if the polypeptide is 6 residues in length, than it can comprise residues including the substitution site (i.e. residue 136 of FGF-1 (residue 122 of SEQ ID NO: 4 or SEQ ID NO: 6), residue 138 of FGF-2).

Sufficient residues are desired to form a good immunogen or blocking antigen for use in assays. It may be desirable to conjugate or genetically fuse additional sequences to the polypeptide, for example, to boost immunogenicity, to enhance purification, to facilitate production or expression, or to facilitate detection. Any sequences as are convenient may be used for these or other purposes. The size of these additional sequences may vary greatly, but typically will be at least 2, 4, 6, or 8 amino acid residues in length. Suitably the additional sequences will be less than 100, 90, 80, 70, 60, 50, 40, 30, 20 or 10 amino acids in length.

A "deletion" in a polypeptide refers to a change in the amino acid sequence which results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a polypeptide refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of a FGF-1 polypeptide may have N-terminal insertions, C-terminal insertions, internal insertions, or any combination of N-terminal insertions, C-terminal insertions, and internal insertions.

Regarding polypeptides, the phrases "percent identity," "% identity," and "% sequence identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

As described herein, variants of the engineered mutant FGF polypeptides disclosed herein may have 99%, 98%, 97%, 96%, 95%, 94%, 93%, 92%, 91%, 90%, 80%, 70%, 60%, or 50% amino acid sequence identity relative to a reference molecule (e.g., relative to the FGF-1 or FGF-2 full-length mutant polypeptides (i.e., SEQ ID NOs: 4, 6, 10, and 12). In some embodiments, variants of the engineered mutant FGF polypeptides disclosed herein may have 99%, 98%, 97%, 96%, 95%, 94%, 93%, 92%, 91%, 90%, 80%, 70%, 60%, or 50% amino acid sequence identity relative to a reference molecule (e.g., relative to the FGF-1 or FGF-2 full-length mutant polypeptides (i.e., SEQ ID NOS: 4, 6, 10, and 12) and include amino acid residue 122 of SEQ ID NO: 4 or SEQ ID NO: 6 or amino acid residue 138 of SEQ ID NO: 10 or SEQ ID NO: 12. Suitably the variants include the substitution mutations identified herein.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The amino acid sequences of the FGF polypeptide variants as contemplated herein may include conservative amino acid substitutions relative to a reference amino acid sequence. For example, a variant, mutant, or derivative FGF polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The amino acid sequences of the FGF polypeptide variants as contemplated herein may include may include modifications made apparent by a sequence alignment of the FGF polypeptides disclosed herein and other FGF polypeptides. A person of ordinary skill in the art, could easily align the FGF polypeptides disclosed herein with FGF polypeptides from, for example, other species to determine what additional variants (i.e. substitutions, insertions, deletions, etc.) could be made to the engineered FGF polypeptides. For example, a person of ordinary skill in the art would appreciate that modifications in a reference FGF polypeptide could be based on alternative amino acid residues that occur at the corresponding position in other homologous FGF polypeptides from other species.

The disclosed FGF polypeptides, mutants, or variants described herein may have one or more functional or biological activities exhibited by a reference polypeptide (e.g., one or more functional or biological activities exhibited by wild-type FGF-1 polypeptide (SEQ ID NO: 2) or wild-type FGF-2 polypeptide (SEQ ID NO: 8)). For example, the disclosed FGF polypeptides, mutants, variants, or derivatives thereof may have increased mitogenic activity or increased stability to protease degradation.

In another aspect of the present invention, fusion proteins are provided. The fusion proteins may include any one of the FGF polypeptides disclosed herein and a membrane permeable peptide. The membrane permeable peptide may be any polypeptide having less than 50, 40, 30, or 20 amino acids that can penetrate cell membranes and deliver conjugated FGF polypeptides into cells. Suitable membrane permeable peptide may include, without limitation, a cell-penetrating polypeptide (CPP), TAT, Pep-1, Penetratin, SynB1, SynB3, PTD-4, PTD-5, Transportan, MAP, SBP, FBP, Polyarginines, or Polylysines.

Polynucleotides encoding any of the FGF polypeptides disclosed herein are also provided. The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

The polynucleotides may encode FGF polypeptides including an R136D substitution of FGF-1, an R136E substitution of FGF-1, a K138E substitution of FGF-2, or a K138D substitution of FGF-2. Suitably the polynucleotides are at least 15, 20, 25, 30, 35, 40, 50, 75, 100, 150, 200, 250, 300, 350, 400, 450, 500 nucleotides long and include the nucleotide coding for the substitution. Suitably the polynucleotide encodes the full-length polypeptide. Polynucleotides encoding partial polypeptides comprising the site of the substitutions indicated are also provided. Polynucleotide sequences of the polypeptides comprising the R136D and R136E substitutions and the wild-type FGF-1 are provided in FIGS. 2-3. The polynucleotide sequences may include the polynucleotide sequences of SEQ ID NO: 3 or SEQ ID NO: 5. Polynucleotide sequences of the polypeptides comprising the K138E and K136D substitutions and the wild-type FGF-2 are provided in FIGS. 14-15. The polynucleotide sequences may include the polynucleotide sequences of SEQ ID NO: 9 or SEQ ID NO: 11.

Isolated polynucleotides homologous to the polynucleotides described herein are also provided. Those of skill in the art also understand the degeneracy of the genetic code and that a variety of polynucleotides can encode the same polypeptide. In some embodiments, the polynucleotides may be codon-optimized for expression in a particular cell such as, without limitation, a mammalian cell or a prokaryotic cell. While particular nucleotide sequences which are found in humans are disclosed herein any nucleotide sequences may be used which encode a desired form of the substituted polypeptides described herein. Thus non-naturally occurring sequences may be used. These may be desirable, for example, to enhance expression in heterologous expression systems of polypeptides or proteins. Computer programs for generating degenerate coding sequences are available and can be used for this purpose as well as other means.

The isolated polynucleotides or polypeptides provided herein may be prepared by methods available to those of skill in the art. Isolated indicates that the polynucleotides or proteins are not in their naturally occurring state. Such preparations may be cell-free preparations. The polynucleotide or polypeptides may be extracted from the cells by breaking the cell membrane and optionally removing non-desired components. The polypeptides may be made as secreted polypeptides and further isolated using means known to those of skill in the art. Alternatively, desired proteins or nucleic acids can be purified using sequence-specific reagents, including but not limited to oligonucleotide probes, primers, and antibodies. Techniques for isolating cell-free preparations are well known in the art, and any that are convenient can be used. The term "substantially isolated or purified" refers to polypeptides or polynucleotides that are removed from their natural environment, and are at least 60% free, preferably at least 75% free, and more preferably at least 90% free, even more preferably at least 95% free from other components with which they are naturally associated.

In another aspect of the present invention, DNA constructs are provided. As used herein, the term "DNA construct" refers to recombinant DNA polynucleotides which may be single-stranded or double-stranded and may represent the sense or the antisense strand. Recombinant polynucleotides are polynucleotides formed by laboratory methods that include polynucleotide sequences derived from at least two different natural sources or they may be synthetic. Constructs thus may include new modifications to endogenous genes introduced by, for example, genome editing technologies. Constructs may also include recombinant polynucleotides created using, for example, recombinant DNA methodologies.

The DNA constructs provided herein may be prepared by methods available to those of skill in the art. Notably each of the DNA constructs claimed are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification and purification. Such techniques are thoroughly explained in the literature.

The DNA constructs provided herein may include a promoter operably linked to any one of the polynucleotides described herein. The promoter may be a heterologous promoter or an endogenous promoter associated with the FGF polypeptide.

As used herein, the terms "heterologous promoter," "promoter," "promoter region," or "promoter sequence" refer generally to transcriptional regulatory regions of a gene, which may be found at the 5' or 3' side of the FGF polynucleotides described herein, or within the coding region of the FGF polynucleotides, or within introns in the FGF polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the disclosed FGF polynucleotides are operably connected to the promoter. As used herein, a polynucleotide is "operably connected" or "operably linked" when it is placed into a functional relationship with a second polynucleotide sequence. For instance, a promoter is operably linked to an FGF polynucleotide if the promoter is connected to the FGF polynucleotide such that it may effect transcription of the FGF polynucleotides. In various embodiments, the FGF polynucleotides may be operably linked to at least 1, at least 2, at least 3, at least 4, at least 5, or at least 10 promoters.

Heterologous promoters useful in the practice of the present invention include, but are not limited to, constitutive, inducible, temporally-regulated, developmentally regulated, chemically regulated, tissue-preferred and tissue-specific promoters. The heterologous promoter may be an animal, plant, bacterial, or fungal promoter. In mammalian cells, typical promoters include, without limitation, promoters for Rous sarcoma virus (RSV), human immunodeficiency virus (HIV-1), cytomegalovirus (CMV), SV40 virus, and the like as well as the translational elongation factor EF-1α promoter or ubiquitin promoter. Other promoters include the T3, T7 and SP6 promoter sequences, which are often used for in vitro transcription of RNA. Those of skill in the art are familiar with a wide variety of additional promoters for use in various cell types. In some embodiments, the heterologous promoter includes a mammalian promoter, either endogenous to the animal host or heterologous.

Vectors, including any of the DNA constructs or polynucleotides described herein, are provided. The term "vector" is intended to refer to a polynucleotide capable of transporting another polynucleotide to which it has been linked. In some embodiments, the vector may be a "plasmid," which refers to a circular double-stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome, such as some viral vectors or transposons. Vectors may carry genetic elements, such as those that confer resistance to certain drugs or chemicals.

Pharmaceutical compositions including any of the FGF polypeptides, polynucleotides, DNA constructs, or vectors described herein are provided. The pharmaceutical compositions may include a pharmaceutical carrier, excipient, or diluent (i.e., agents), which are nontoxic to the cell or mammal being exposed thereto at the dosages and concentrations employed. Often a pharmaceutical agent is in an aqueous pH buffered solution. Examples of pharmaceutical carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

Hydrogels including any of the FGF polypeptides, polynucleotides, DNA constructs, or vectors described herein are provided. Suitably, the hydrogels include any one of the FGF polypeptides disclosed herein. As used herein, a "hydrogel" refers to a gel in which the liquid component is water.

Methods of treating a condition are also provided. The methods may include administering any of FGF polypeptides, polynucleotides, DNA constructs, vectors, pharmaceutical compositions, or hydrogels described herein to a subject in an amount effective to treat the condition. The condition may include a wound (chronic and acute), Type 1 diabetes, Type 2 diabetes, obesity, internal injuries, a cardiovascular disorder, a cosmetic condition (i.e. whitening, wrinkling), critical limb ischemia, a nerve injury, a burn, hair loss (whether genetic or not, i.e. alopecia), a retinal disorder (i.e., retinopathy disorders), a muscular disorder, an arterial disease, an age related disorder, organ or tissue damage (whether or not from chemotherapy or radiation therapy), osteoporosis, a digestive tract ulcer (i.e., gastric ulcer), ulcerative colitis, a scar, an energy homeostasis disorder such as obesity, dyslipidemia, diabetes, insulin resistance, hyperglycemia or the metabolic syndrome, osteoarthritis, and acute renal failure.

The subject may be any mammal, suitably a human, domesticated animal such as a dog, cat, horse, cow, pig, or a mouse or rat. Treating the condition or treatment includes but is not limited to ameliorating at least one symptom of the condition, reducing or slowing further progression of the condition, reducing or slowing the spread of the condition to unaffected areas. Treating a subject refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

An effective amount or a therapeutically effective amount as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions (i.e. FGF polypeptides, polynucleotides, DNA constructs, vectors, pharmaceutical compositions, or hydrogels) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, intra-lesional, intra-tumoral, intradermal, or transmucosal absorption. Thus the compositions may be formulated as an ingestible, injectable, topical or suppository formulation. The compositions may also be delivered with in a liposomal or time-release vehicle. The methods may also include an electrical stimulation or electroporation step to aid entry of the polypeptides, polynucleotides, or pharmaceutical compositions into the intracellular space. Administration of the compositions to a subject in accordance with the invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol.

The maximal dosage for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will improve wound healing or other condition being treated by at least 10%, 20%, 30%, 40%, 50%, 60%, 70%, 80%, 90%, 100% or more as compared to no treatment.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The FGF polypeptides, polynucleotides, DNA constructs, vectors, pharmaceutical compositions, or hydrogels described herein may be administered one time or more than one time to the subject to effectively improve wound healing or other condition being treated. Suitable dosage ranges are of the order of several hundred micrograms effective ingredient with a range from about 0.01 to 10 mg/kg/day, preferably in the range from about 0.1 to 1 mg/kg/day. Precise amounts of effective ingredient required to be administered depend on the judgment of the practitioner and may be peculiar to each subject. It will be apparent to those of skill in the art that the therapeutically effective amount of the polypeptides, polynucleotides, and pharmaceutical compositions described herein will depend, inter alia, upon the administration schedule, the unit dose of antigen administered, whether the composition is administered in combination with other therapeutic agents, the status and health of the recipient, and the therapeutic activity of the particular composition.

Given that the FGF polypeptides of the present invention confer greater resistance to proteases and higher biological activity, it is envisioned that compositions including or encoding such polypeptides would be useful in several different FGF applications.

In some embodiments, the FGF compositions described herein (either individually or in combination) may be used to treat diabetes (i.e., type 1 or type 2). Treatment of type1 and type2 diabetes may be achieved by injecting the FGF compositions (either individually or in combination). Without being limited by theory, systemic FGF polypeptides could potentially activate the process of angiogenesis. Also the skeletal muscle cell multiplication drastically increases that could result in large uptake of blood glucose eventually restore the pancreas to function normally.

In some embodiments, the FGF compositions described herein (either individually or in combination) may be used to treat internal injuries. Because the disclosed FGF polypeptides demonstrated protease resistant activity, they may be used in treating visceral injuries such as intestinal wall ruptures (sites with excess protease action like trypsin etc.).

In some embodiments, the FGF compositions described herein (either individually or in combination) may be used in cosmetic applications. For example, a medicinal composition including the FGF compositions described herein (either individually or in combination) and FGF2, FGF5, FGF7 and/or FGF10 could be used in various cosmetic applications including, without limitation, whitening, anti-crinkle and anti-aging related problems.

In some embodiments, the FGF compositions described herein (either individually or in combination) may be used to treat cardiovascular disorders. It has been shown that injection of FGF-1 into the intramyocardial region resulted in improved collateral artery growth and capillary formation and proliferation. Thus, the FGF compositions (either individually or in combination) may be used to improve collateral artery growth and capillary formation and proliferation.

In some embodiments, the FGF compositions described herein (either individually or in combination) may be used to treat critical limb ischemia. For example, gene therapy based delivery of FGF polypeptides (either individually or in combination) could be used in treating end stage limb ischemia which would potentially reduce the chances of amputation.

In some embodiments, the FGF compositions described herein (either individually or in combination) may be used in treating nerve injuries. The disclosed FGF compositions (either individually or in combination) could be used to regenerate damaged cells in the spinal cord.

In some embodiments, the FGF compositions described herein (either individually or in combination) may be used to treat burns. Several factors are responsible for causing burns such as heat, electricity, UV-light and corrosive chemicals. The disclosed FGF compositions (either individually or in combination) might quicken the process of healing of burns along with other pharmacologically active ingredients.

In some embodiments, the FGF compositions described herein (either individually or in combination) may be used in hydrogels. Hydrogels including the disclosed FGF compositions (either individually or in combination) could be used in design and development of scaffolds in the fields of tissue engineering and regenerative medicine.

In some embodiments, the FGF compositions described herein (either individually or in combination) may be used in regenerating hair growth. Growth factors like FGF1, FGF2, and FGF10 are known to be involved in the regulation of hair morphogenesis and hair growth. Due to the enhanced bioactive properties of the disclosed FGF compositions, the disclosed FGF compositions may be used to alter (increase or decrease) hair growth.

In some embodiments, the FGF compositions described herein (either individually or in combination) may be used to treat wounds. For example, compositions including Parathyroidharmone (PTH), Collagen binding protein (CBD), and the disclosed FGF compositions (either individually or in combination) could be used in the treating both chronic and acute wounds.

In some embodiments, the FGF compositions described herein (either individually or in combination) may be used to repair an injured retina. The disclosed FGF compositions (either individually or in combination) may be used for rejuvenating damaged cells of the retina such as in retinopathy disorders.

In some embodiments, the FGF compositions described herein (either individually or in combination) may be used in skeletal muscle development. For example, the disclosed FGF compositions (either individually or in combination) could be fused to other FGF family members that could facilitate the faster growth of skeletal muscle.

In some embodiments, the FGF compositions described herein (either individually or in combination) may be used in cell cultures such as mammalian cell cultures.

In some embodiments, the FGF compositions described herein (either individually or in combination) may be used to treat arterial diseases. For example, the disclosed FGF compositions (either individually or in combination) may be used in treatment of peripheral arterial disease with intermittent claudication.

In some embodiments, the FGF compositions described herein (either individually or in combination) may be used to treat aging related disorders.

In some embodiments, the FGF compositions described herein (either individually or in combination) may be used to regenerate internal organs.

In some embodiments, the FGF compositions described herein (either individually or in combination) may be used to treat osteoporosis.

In some embodiments, the FGF compositions described herein (either individually or in combination) may be used to treat gastric ulcers.

In some embodiments, the FGF compositions described herein (either individually or in combination) may be used to treat colitis such as ulcerative colitis. For example, the disclosed FGF compositions (either individually or in combination) may be used in combination with keratinocyte growth factor-1 to treat ulcerative colitis.

In some embodiments, the FGF compositions described herein (either individually or in combination) may be used to treat scars developed from various types of injuries.

In some embodiments, the FGF compositions described herein (either individually or in combination) may be used in combination with biopolymers such as carboxy methyl benzyamine dextran sulfonate to treat digestive tract ulcers.

In some embodiments, the FGF compositions described herein (either individually or in combination) may be used to affect differentiation of osteoblast cells. For example, the disclosed FGF compositions (either individually or in combination) may be used, for example by gene therapy, to enhance the down regulation of Wnt signaling proteins which would result in decreased differentiation of osteoblast cells.

In some embodiments, the FGF compositions described herein (either individually or in combination) may be used to treat damaged tissue due to radiation or chemotherapy. For example, the disclosed FGF compositions (either individually or in combination) may be used in combination with FGF-20 to treat damaged tissue due to radiation and also due to extensive use of chemotherapy.

In some embodiments, the FGF compositions described herein (either individually or in combination) may be used to treat diabetes and obesity. For example, FGF-21 controls the glucose-uptake of adipocytes independent of insulin which would decrease the load of blood glucose, triglycerides and glucagon. Thus, compositions including the FGF compositions described herein (either individually or in combination) and FGF-21 would be used in treating diabetes and obesity.

In some embodiments, the FGF compositions described herein (either individually or in combination) may be used to treat disorders related to energy homeostasis. For example, the disclosed FGF compositions (either individually or in combination) may be used in combination with FGF8 to treat disorders of energy homeostasis such as obesity, dyslipidemia, diabetes, insulin resistance, hyperglycemia or the metabolic syndrome.

In some embodiments, the FGF compositions described herein (either individually or in combination) may be used to control differentiation of cord cells. For example, the disclosed FGF compositions (either individually or in combination) may be used in combination with FGF4 to induce human umbilical cord mesenchymal stem cells to differentiate into hepatocytes.

In some embodiments, the FGF compositions described herein (either individually or in combination) may be used to treat alopecia. For example, the disclosed FGF compositions (either individually or in combination) may be used in combination with FGF-10 to treat alopecia.

In some embodiments, the FGF compositions described herein (either individually or in combination) may be used to treat osteoarthritis. For example, the disclosed FGF compositions (either individually or in combination) may be used in combination with FGF-9 to promote cartilage repair in patients suffering from osteoarthritis by reducing the abnormal differentiation of articular cartilage cells at the site of inflammation.

In some embodiments, the FGF compositions described herein (either individually or in combination) may be used to treat acute renal failure. For example, the disclosed FGF compositions (either individually or in combination) may be used in combination with inhibin beta and FGF-2 to treat acute renal failure.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Materials and Methods
Polymerase Chain Reaction

Polymerase chain reaction (PCR) for amplification and generation of FGF1 mutant plasmid DNA was performed using a QuikChange Site-Directed Mutagenesis Kit. The reaction mixture consisted of 1 pmol each of forward & reverse primers, 5 uL of 10× Pfu reaction buffer, 1 uL dNTP, 10-15 ng of wild-type plasmid DNA, 1 uL Pfu DNA polymerase and autoclaved deionized water to give a total volume of 50 uL. Cycling parameters were as per the manufacturer's instructions.

After PCR, the reaction mixture was subjected to Dpn1 digestion to eliminate the methylated parental DNA. Mutant pDNA was used to transformed cXL1-Blue supercompetent cells. Plasmid extraction was performed using a QIAprep Spin Miniprep Kit (250), and the correctness of DNA was verified by DNA sequencing.

FGF-1 Expression

The expression of wt and mutant FGF-1 proteins was achieved by transforming B121DE3 PlysS *Escherichia coli* with the wt and mutant FGF1 plasmid DNA and the transformed expression host cells were grown in LB medium. $^{15}$N-labeled protein was prepared by growing the cells in M9-minimal medium containing $^{15}$N-labeled $NH_4Cl$ as the sole source of nitrogen. Induction with isopropyl β-D-1-thiogalactopyranoside (IPTG) was performed when the optical density (O.D.) of the inoculated medium was between 0.5-0.6. Cells were harvested by centrifugation and resuspended in buffer containing 10 mM phosphate, 1 mM EDTA, 0.1% beta-mercaptoethanol, and 1 mM PMSF at a pH of 7.2.

FGF-1 Purification

The purification of FGF-1(wt) and the FGF-1 mutant proteins was performed on heparin-sepharose affinity column. Pure protein was obtained using 10 mM phosphate buffer, pH 7.2, with an increasing sodium chloride concentration in a step-gradient manner. FGF-1(wt) and mutant proteins eluted at different salt concentrations based on their affinity toward the immobilized heparin moiety. Purity of the protein was confirmed by resolving the samples on 15% SDS-PAGE. All purified protein samples were subjected to dialysis against a buffer of 10 mM phosphate, 100 mM NaCl, 50 mM ammonium sulfate, pH 6.5.

Mitogenic Activity

The mitogenic activities of WT FGF-1 and all mutants were determined through cell proliferation assays using NIH-3T3 mouse embryonic fibroblast cells maintained in tissue culture under specific conditions (37° C. and 7% $CO_2$). Dulbecco's Modified Essential Medium (DMEM)

containing 10% newborn calf serum (NCS), L-Glutamine, and penicillin were used to grow the fibroblast cells. After the cells reached a confluency rate of 80%, they were diluted and an appropriate amount of the cell culture was transferred to a new flask to continue their growth. In a 96-well plate, approximately 4000 cells/80 μL of media were added. The well plate was then incubated for 24 hours in absence and presence of heparin and also with the fixed concentrations of wt and mutant FGF1 proteins in order for the cells to adhere to the bottom of the plate. After the 24-hour time period, the medium was removed, the cells were rinsed with PBS, and the medium was replaced with DMEM with 0.5% NCS starvation medium and incubated for another 18 to 24 hours. A Biotek EL808 microplate reader was used to determine the absorbance of the wells in the well plate at 450 nm.

Limited Trypsin Digestion and Thrombin Cleavage

Limited proteolytic digestion experiments were performed at 37° C. using trypsin (Sigma) as the proteolytic enzyme in the absence and presence of sucrose octasulfate. Proteolytic digestions were carried out by adding 100 units of enzyme to 1 mL of 37.5 μM FGF-1. The reaction was stopped at 5-minute time intervals by the addition of saturated trichloroacetic acid (TCA). The degree of proteolytic cleavage was estimated by densitometry of the intensity of the 16 kDa band corresponding to the undigested FGF-1. The intensity of the FGF-1 band prior to the addition of trypsin was used as 100% undigested protein.

Differential Scanning Calorimetry

Differential Scanning calorimetry was performed on an N-DSC III Differential Scanning calorimeter. The concentration of protein was 75 uM in 10 mM phosphate, 100 mM NaCl, 50 mM ammonium sulfate, pH 6.5. Scans were performed from 10-90° C. with 1° C./min ramping temperature. Data was plotted using CpCalc Version 2.2.0.10 software supplied by the manufacturer.

2D $^1$H-$^{15}$N HSQC NMR Spectroscopy

NMR experiments were performed on a Bruker Avance DMX-700 MHz spectrometer equipped with a 5 mm inverse cryoprobe at 25° C. $^{15}$N labeled protein samples were prepared in 10 mM phosphate, 100 mM sodium chloride, 50 mM ammonium sulfate, pH 6.5 added with 10% D2O. The data was analyzed using XWINNMR 3.5 software supplied by Bruker.

Isothermal Titration Calorimetry of the FGF-1 Mutants with SOS

The binding of FGF-1(wt) and the mutants with SOS was monitored by measuring the heat changes during the titration of SOS into the cell containing FGF-1 using a Microcal VP-ITC MicroCalorimeter. For WT hFGF-1, and mutant proteins were in the cell and at a concentration of 0.05 mM in a buffer of 10 mM phosphate, 100 mM NaCl, 50 mM ammonium sulfate, pH 6.5. The SOS in the syringe was at a concentration of 0.5 mM in a buffer of 10 mM phosphate buffer (pH 6.5) containing 100 mM NaCl and 50 mM ammonium sulfate. The volume of SOS injections was 6 uL and injections were continued every 5 minutes for a total of 49 injections at 25° C. The data was analyzed using Origin scientific plotting software.

Western Blot Analysis of Phosphaorylated Forms of Akt and ERK Proteins

NIH 3T3 cells grown in DMEM and after starvation the cells were added with fixed concentration of buffer blank, WT and mutant FGF1 proteins. Cells were harvested by centrifugation at 1500×g and lysed. Samples were resolved on SDS-PAGE and the proteins were transferred on to a nitrocellulose membrane. Phosphorylated Akt and ERK proteins were detected by using specific polyclonal antibodies. Densitometry of the bands was plotted as the relative difference in expression of the phosphorylated protein.

Endothelial Migration/Wound Healing Assay

A line was drawn at the bottom of 6 well plates for indication of where to make the scratches and for orientation during microscopy. Murine 2H11 endothelial cells were cultured to near confluency (~70-90%) in 6 well dishes over night, then rinsed and put in starvation media (0.5%-0.1% serum) for 24 hrs. Using a sterile 200 μl or 1000 μl pipette tip, three scratches were made through the cells perpendicular to the previously drawn line. The cells were rinsed gently with serum free medium and then 1.5 ml medium with 2, 20, or 40 μg/ml of wild type or mutant FGFs was added. Pictures were taken at 0, 6, 12, 24 and 48 hrs (phase contrast-10×) of the scratches and the width of the scratch was measured (at 6 and 12 hrs fresh medium containing FGFs was also re-added). For data analysis, each scratch diameter was subtracted from the baseline diameter and the percent that the diameter of the scratch decreased was calculated.

Results

The 3D structure of FGF-1 shows residues important for binding to the fibroblast growth factor receptor molecule (FGFR1) and residues that binds to heparin. See, e.g., FIG. 4. It is known that FGF-1 shows a stretch of positive amino acids at the C-terminus side of the molecule that is important for binding to heparin. One of those residues R136 is critical and also sensitive to secondary proteolytic degradation by thrombin. Therefore, using site-directed mutagenesis protocol, wtFGF-1 was subjected to mutation at position 136 whereby residue arginine was replaced to glutamic acid. This new recombinant vector containing nucleic acid sequence of mutated FGF-1 codes for mutated form of FGF-1 with glutamic acid instead of arginine at position 136. The translated protein product with the above substitution showed an increased resistance to degradation by thrombin and an enhanced biological activity compared to the wtFGF-1. Wound healing assay using Swiss 3T3 cells showed a striking difference between wtFGF-1 and R136E. Cells treated with wtFGF-1 exhibited epithelioid cobblestone-like morphology even at the migrating front of monolayer wounds, while mutant FGF-1R136E induced spindle-like or triangular cell shapes, and cells migrated individually, not as a defined front. Because of different characters of wound closing, we assessed cell migration by number of cells, which reached median areas of the wounds. We found that by 40 hours after wounding the presence of cells in the central wound areas was at least twice higher with mutant FGF-1R136E than with wtFGF-1.

To generate the mutation, following bases were changed in the wtFGF-1

1.
(SEQ ID NO: 13)
5'TGCAAACGCGGTCCT<u>CGG</u>ACTCACTATGGCCAG 3'-wtFGF 2.
(SEQ ID NO: 14)
5'TGCAAACGCGGTCCT<u>GAG</u>ACTCACTATGGCCAG 3'-R136E 3.
(SEQ ID NO: 15)
5'TGCAAACGCGGTCCT<u>AAG</u>ACTCACTATGGCCAG 3'-R136K

Effects of Mutations on Mitogenic Activity of FGF-1

Mitogenic assay was performed to determine the cell proliferation activity of wild-type FGF-1 and mutant proteins. FIG. 5 shows the activity of WT FGF-1 and each mutant as a measure of number of cells multiplied. Although some mutants were less active, all showed some degree of activity. Interestingly, R136E showed higher activity compared to WT FGF-1 or any of the other mutants tested. This could be a result of the increased stability R136E mutation conferred to the FGF1 molecule. R136E mutant showed an increased thermal stability, resistance to proteolytic digestion. Despite the decrease in heparin-binding affinity, R136E is most active, suggesting heparin-binding may not be a requirement for FGF-1 signaling.

Effects of Mutations on Proteolytic Digestion of FGF1

Figure 6A:
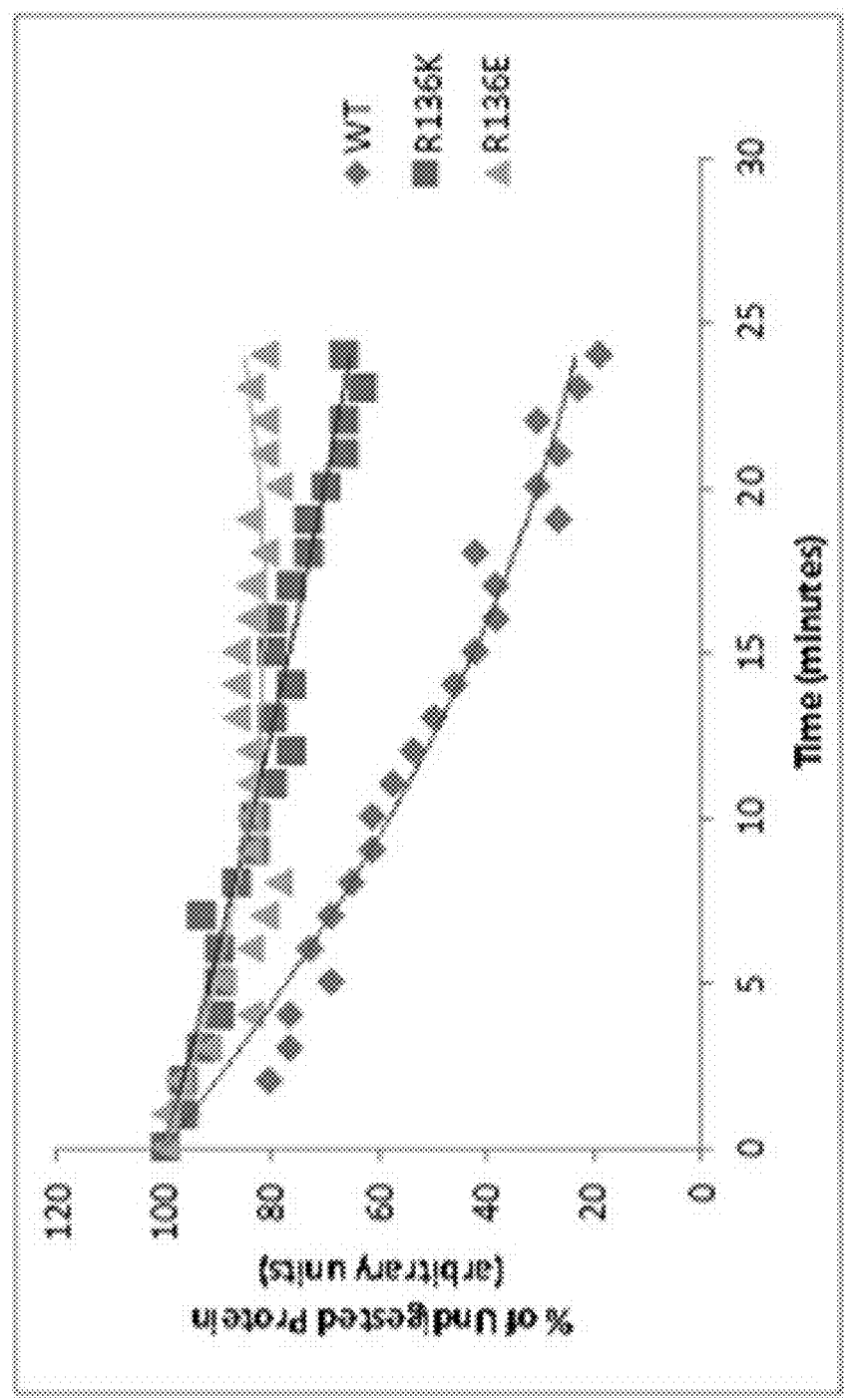
FIG. 6 shows graphs of the thrombin cleavage activity of wildtype (wtFGF-1), R136K and R136E mutants of FGF-1 in the absence and presence of SOS (sucrose octa sulfate an analog for heparin). When compared with wtFGF-1, R136K and R136E mutants show minimal degradation both mutant or variant forms. As used herein, a "variant" refers to a polypeptide molecule having an amino acid sequence that differs from a reference protein or polypeptide molecule. A variant may have one or more insertions, deletions, or substitutions of an amino acid residue relative to a reference molecule. A variant may include a fragment of a reference molecule. For example, a FGF polypeptide variant molecule may have one or more insertions, deletions, or substitution of at least one amino acid residue relative to the mutant FGF polypeptides described herein.
Figure 6B:
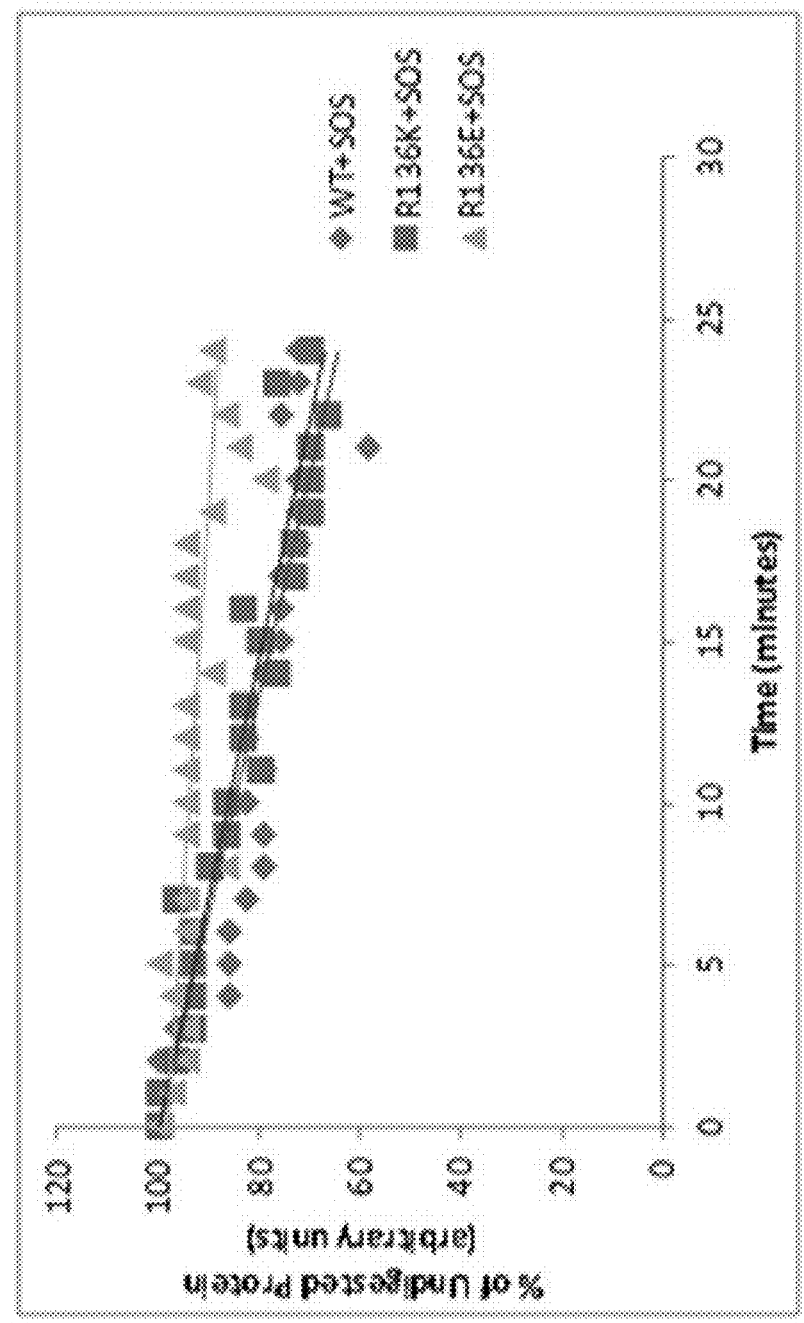
Figure 7A:
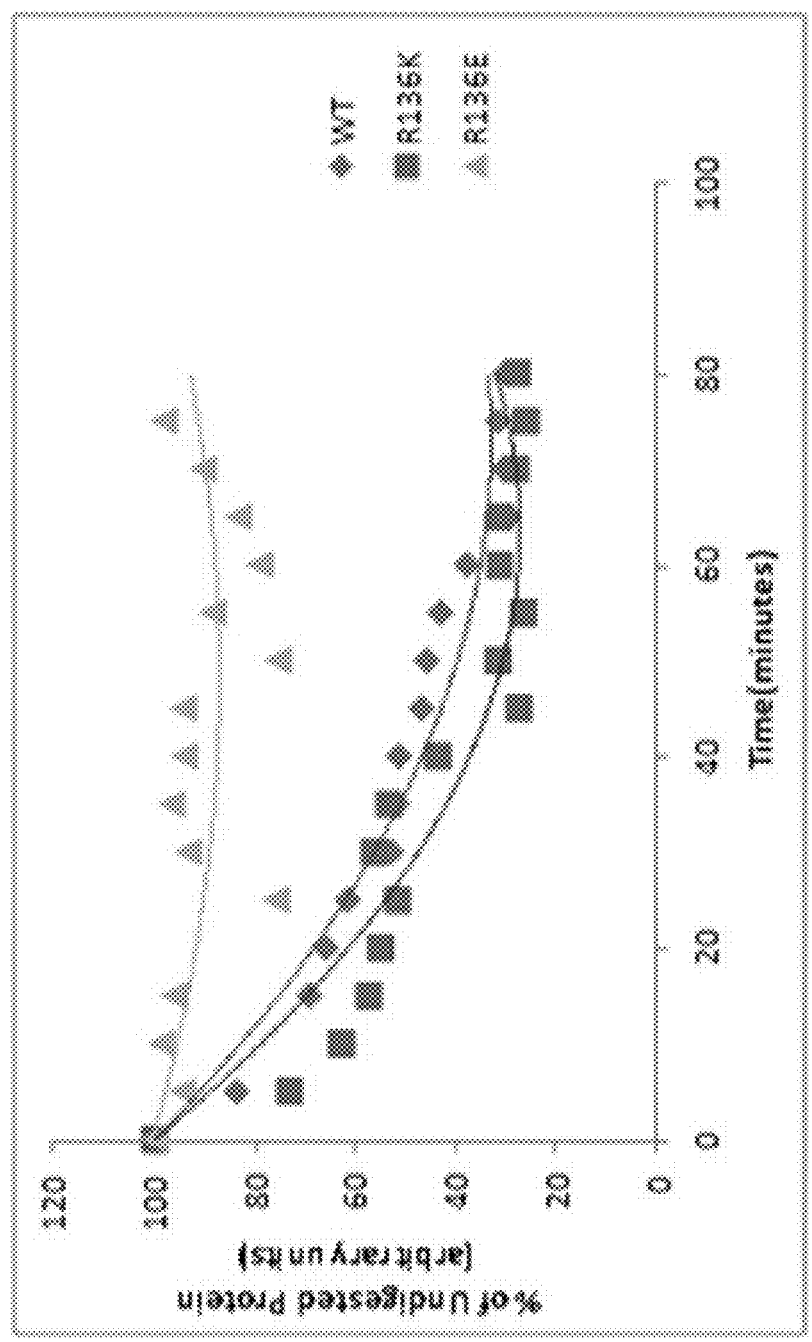
Figure 7B:
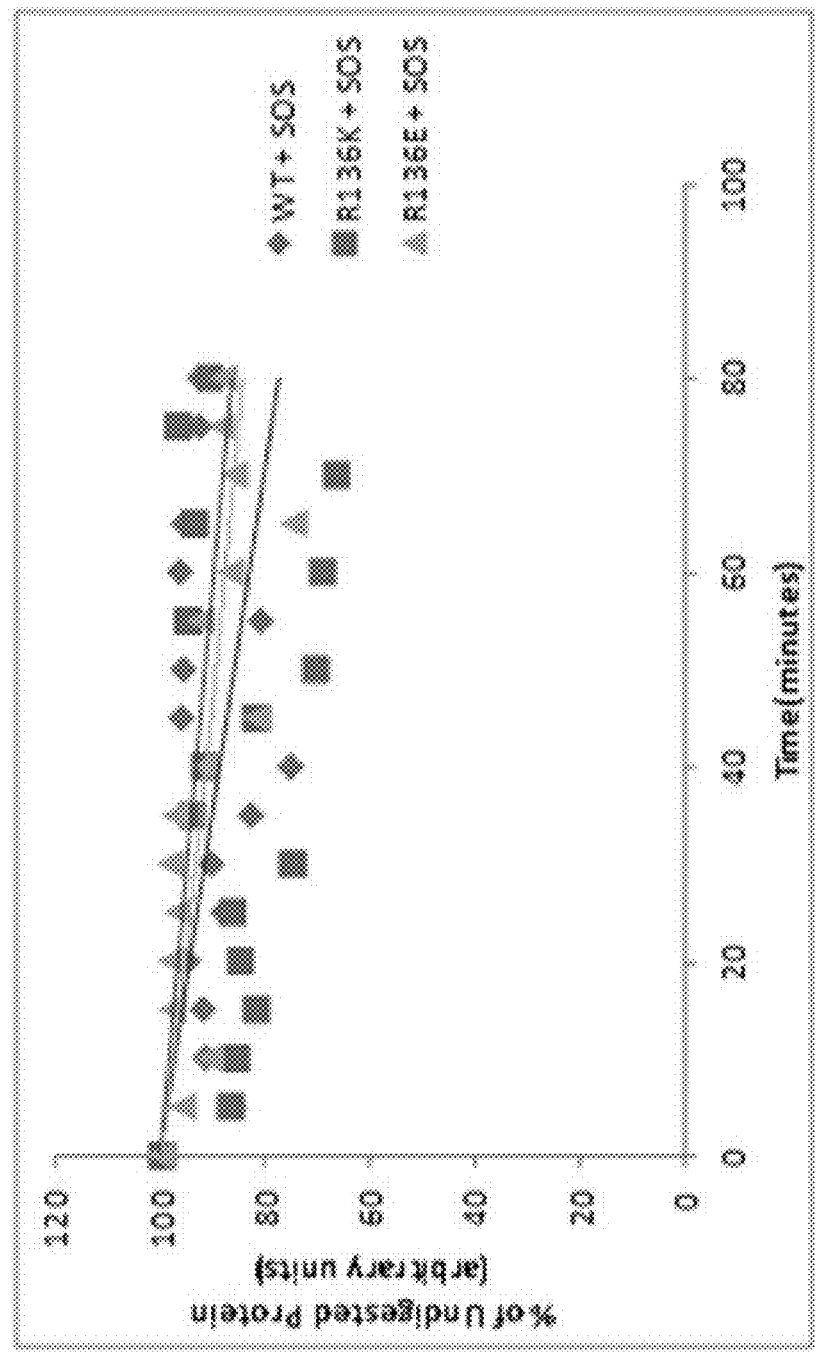

To determine the effects of the charge-reversal mutations on solvent exposure and stability against enzymatic cleavage, resistance to trypsin and thrombin proteases was performed both in the absence and presence of SOS at 37° C. FIG. 6 and FIG. 7 shows the percentage of undigested hFGF-1 versus time for wt hFGF-1, R136K, R136E in the absence and presence of SOS. The degree of proteolytic cleavage was determined by densitometric analysis of the 16 kDa band corresponding to the undigested hFGF-1; the intensity of the hFGF-1 band prior to the addition of trypsin corresponds to 100% undigested protein. In the absence of SOS, ~40% of the WT hFGF-1 remains intact after incubation with trypsin for 60 minutes. FGF1-R136E mutant was significantly more stable in the presence of trypsin and thrombin than WT: after 1 hour, ~80% of R.136E remained uncleaved compared to ~40% of WT showed an increased protease resistance compared to wt and R136K mutant. Also R136E mutant showed no significant difference in the absence and presence of heparin this supports the mitogenic data where the R136E showed higher activity in the absence of heparin.

Effects of Mutations on Thermal Stability of FGF1

Figure 8A:
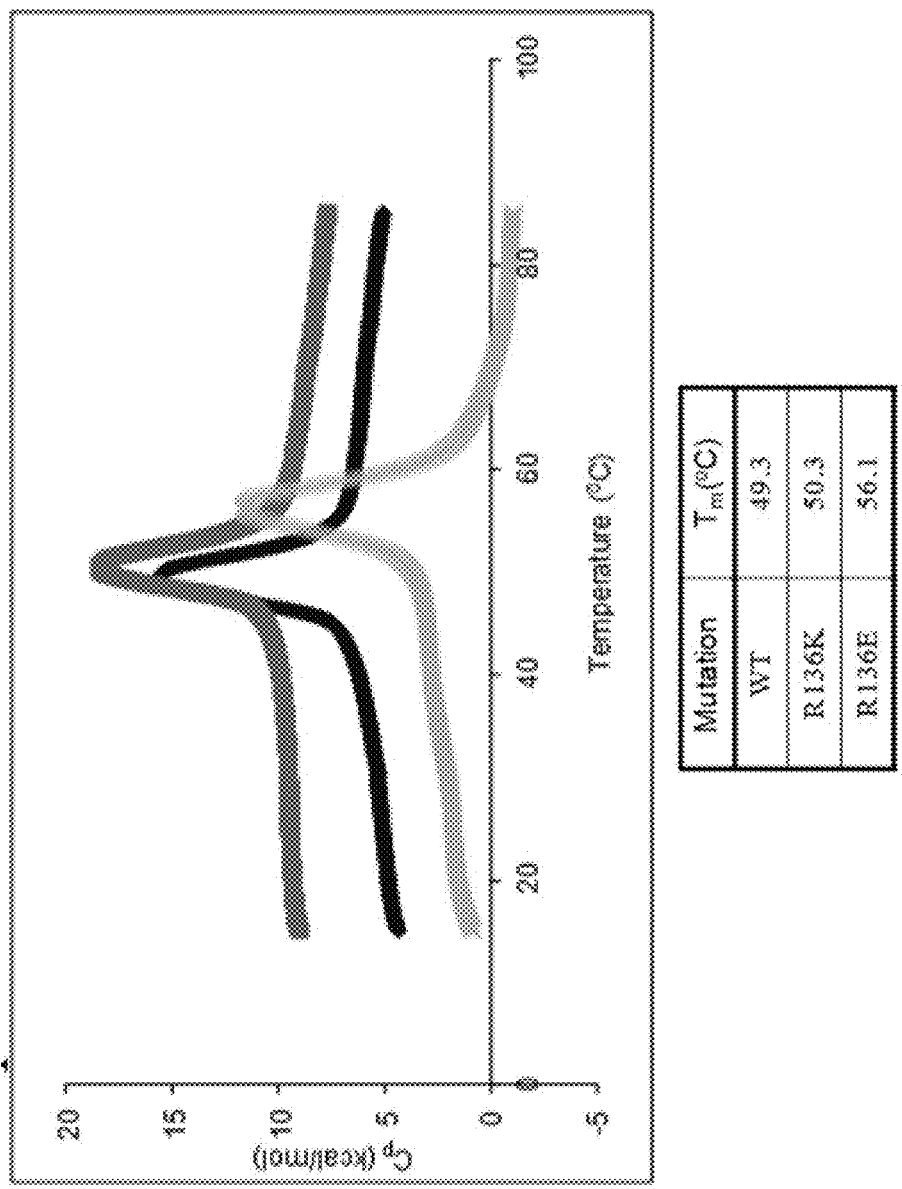
Figure 8B:
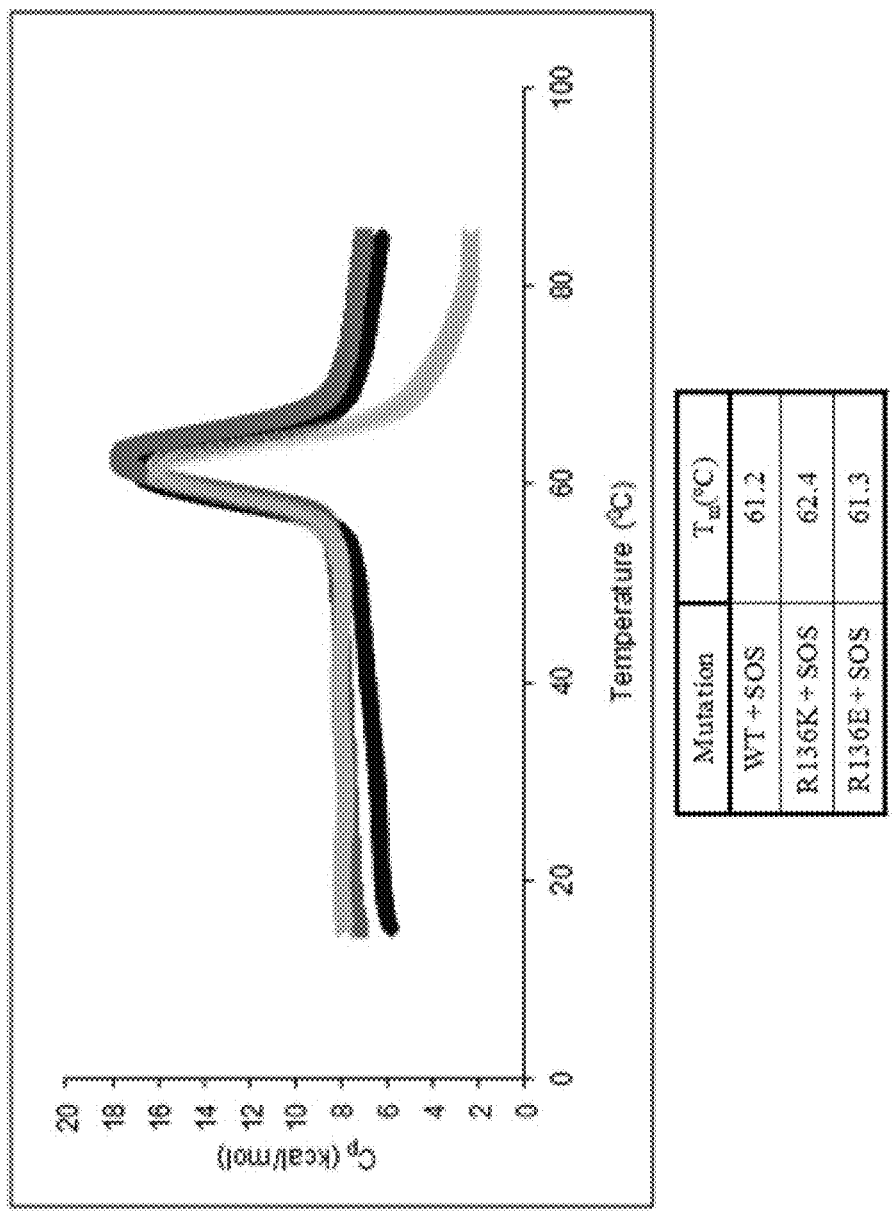

Differential Scanning calorimetry (DSC) directly measures the thermal stability of a protein. DSC was performed to determine the melting temperature ($T_m$) of WT hFGF-1 and mutation alone and in the presence of sucrose octasulfate (SOS). The changes in $T_m$ values are reflective of the effect the mutant has on the thermal stability of the protein as well as the effect the mutation has on the SOS binding affinity. The $T_m$ value of WT hFGF-1 was 49.3° C. in the absence of SOS; this value increased to 61.12° C. when 0.5 mM SOS was added, giving a $\Delta T_m$, of 11.9° C. (FIG. 8). Compared to R136K, R136E mutant showed an increase in thermal stability of over 6° C. compared to wtFGF1 in the absence of heparin. However, the $T_m$ values were similar in the presence of SOS resulting in a lower $\Delta T_m$, value of R136E (5.2° C.), reflective of some loss of SOS/heaprin affinity observed in ITC FIG. 8).

Although it was originally expected that inserting a negatively charged amino acid among several positively charged residues would result in increased stability (due to the possible formation of salt bridges), the DSC results have shown the opposite, with the exception of R136E. The reason for this observation may be due to the distances between the inserted negative charge and the surrounding positive residues. Although the formation of a salt bridge increases stability, the oppositely charged amino acids must be within 5 Å of each other, otherwise long-range electrostatic interactions can occur, which are often destabilizing. (Kumar and Nussinov 2002). For instance, in a study of 22 ion pairs in 14 NMR conformer ensembles for 11 nonhomologous proteins, 92.1% of salt bridges, 68% of N—O bridges, and only 33% of longer-range ion pairs were stabilizing, likely because close-range electrostatic interactions have a more favorable geometrical orientation and electrostatic strength (Kumar and Nussinov 2001; Kumar and Nussinov 2002). Mutation of R136 to glutamic acid would result in the formation of salt bridge which might contribute to the increased stability.

Effect of Muattions on the Amino Acid Perturbrations in FGF1

Figure 9:
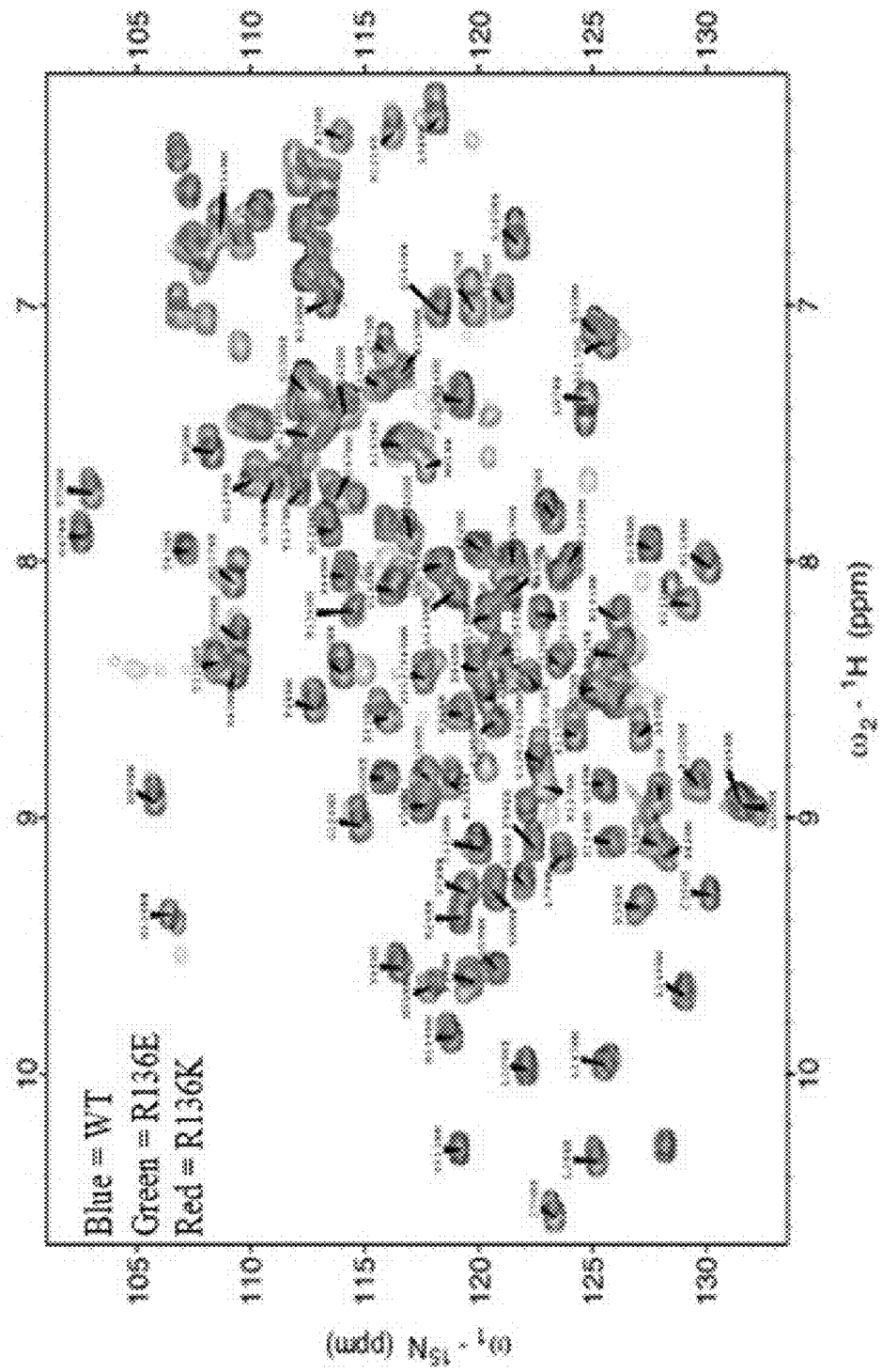

NMR spectroscopy is useful for the determination of residues involved in ligand binding as well as the conformational changes of a protein caused by a mutation. 2D $^1H$-$^{15}N$ HSQC NMR spectra were acquired for WT hFGF-1 and all mutants in the absence and presence of SOS. An overlay of WT hFGF-1 with each mutant reveals the residues shifted due to the mutation (FIG. 9), while the overlay of the spectra for each mutant in the presence of SOS shows the residues that shift upon binding to SOS. R136E (data not shown) have a perturbation plot similar to that of WT overlaid with WT in the presence of SOS. This indicates that the binding between R133E and R136E to SOS is not greatly affected by the mutation.

Effects of Mutations on Heparin Binding Affinity of FGF1

Figure 10A:
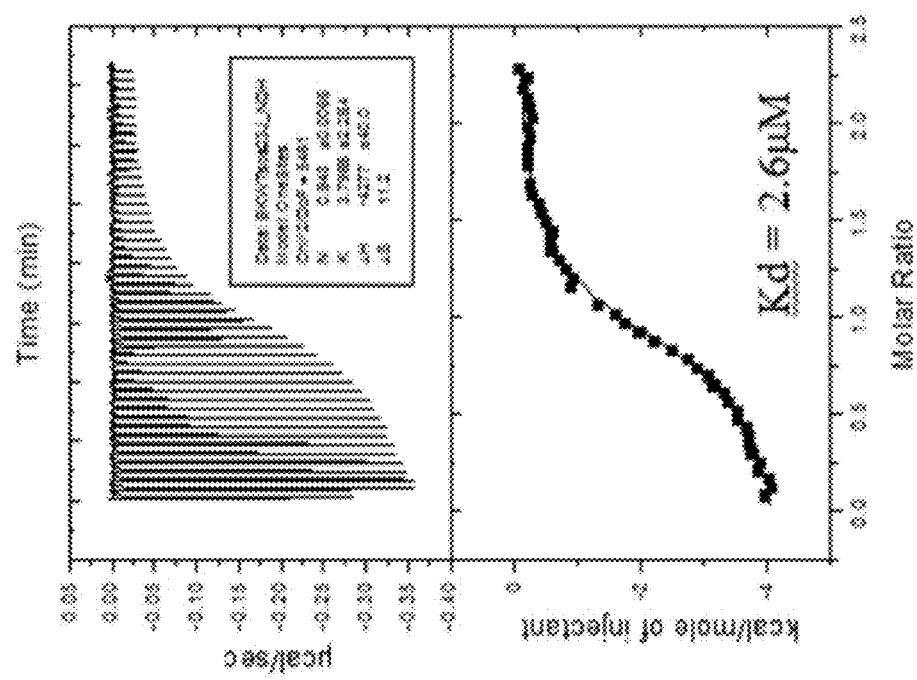
Figure 10B:
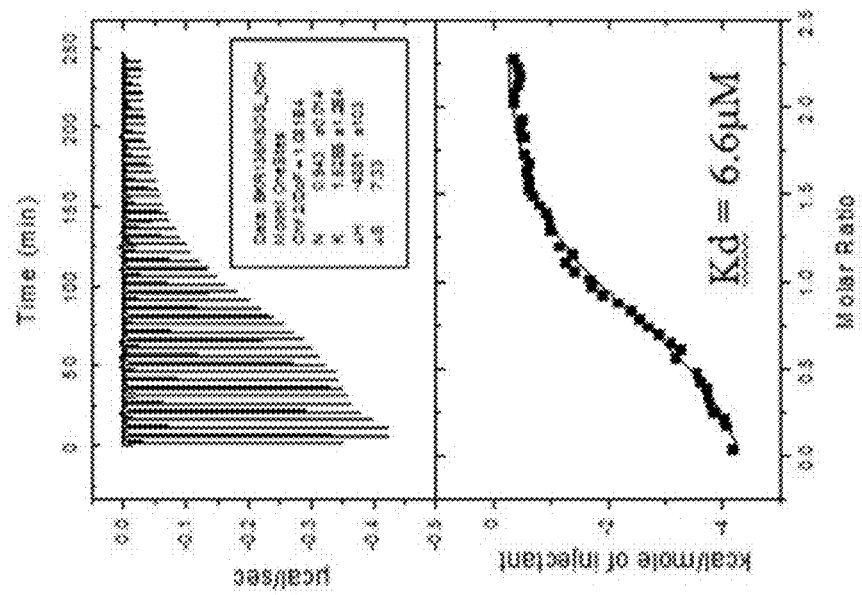
Figure 10C:
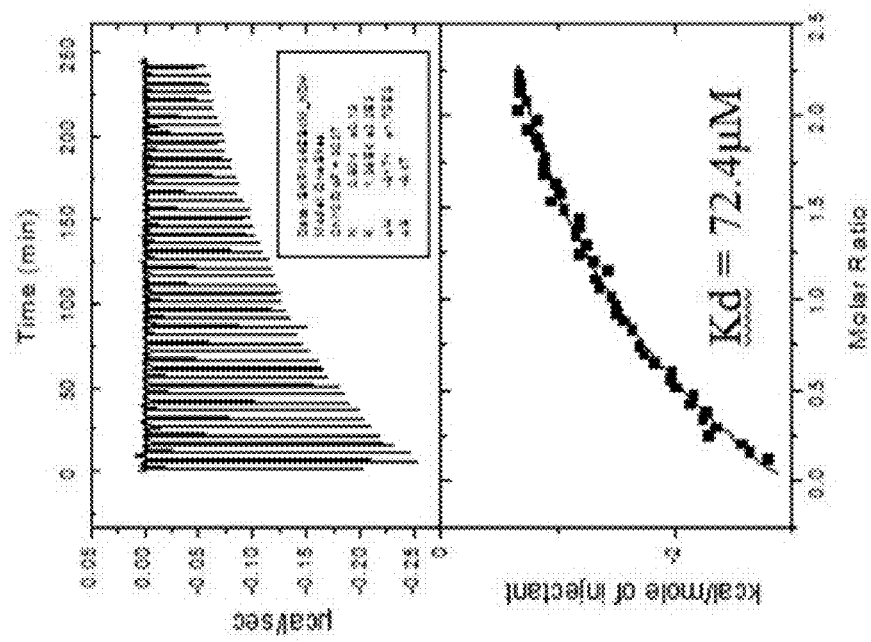

The method used to study the affinities of WT hFGF-1 and each mutant for heparin and the heparin analog, sucrose octasulfate (SOS), was Isothermal Titration calorimetry (ITC). ITC is a method used to directly evaluate the affinity and enthalpy of binding reactions. The dissociation constant ($K_d$) obtained from the isotherm represents the affinity of the protein to SOS or heparin; the binding event for both found to be exothermic. The $K_d$ value for wt hFGF-1 was 2.6 μM for SOS (FIG. 10A). R136E showed a significant decrease in binding with $K_d$ values of 72.4 μM (FIG. 10C) for SOS and 16.72 μM for heparin (data not shown) confirms the charge reversal effect on heparin binding affinity. R136K showed a $K_d$ for SOS similar to that of WT (FIG. 10B) as the basic amino acid arginine replaced with another basic amino acid lysine. This indicates that, although each mutant falls within the heparin binding region of hFGF-1, they each contribute differently to the binding.

Effect of Mutations on the Phosphorylation of Akt and ERK Proteins

FGF1 is known to activate various cellular pathways upon binding to FGF receptor. Two important pathways among them Akt and ERK1/2 are critical for apoptosis and cell differentiation. FGF1-R136 mutant showed a marginal difference in phosphorylation of Akt and ~four fold increase in the ERK protein phosphorylation compared to that of WT. See FIG. 11. This confirms that the increased stability of the protein has a drastic effect on the cell proliferation property of this mutant protein.

Effect of Mutations on Wound Healing Property of FGF1

Figure 12C:
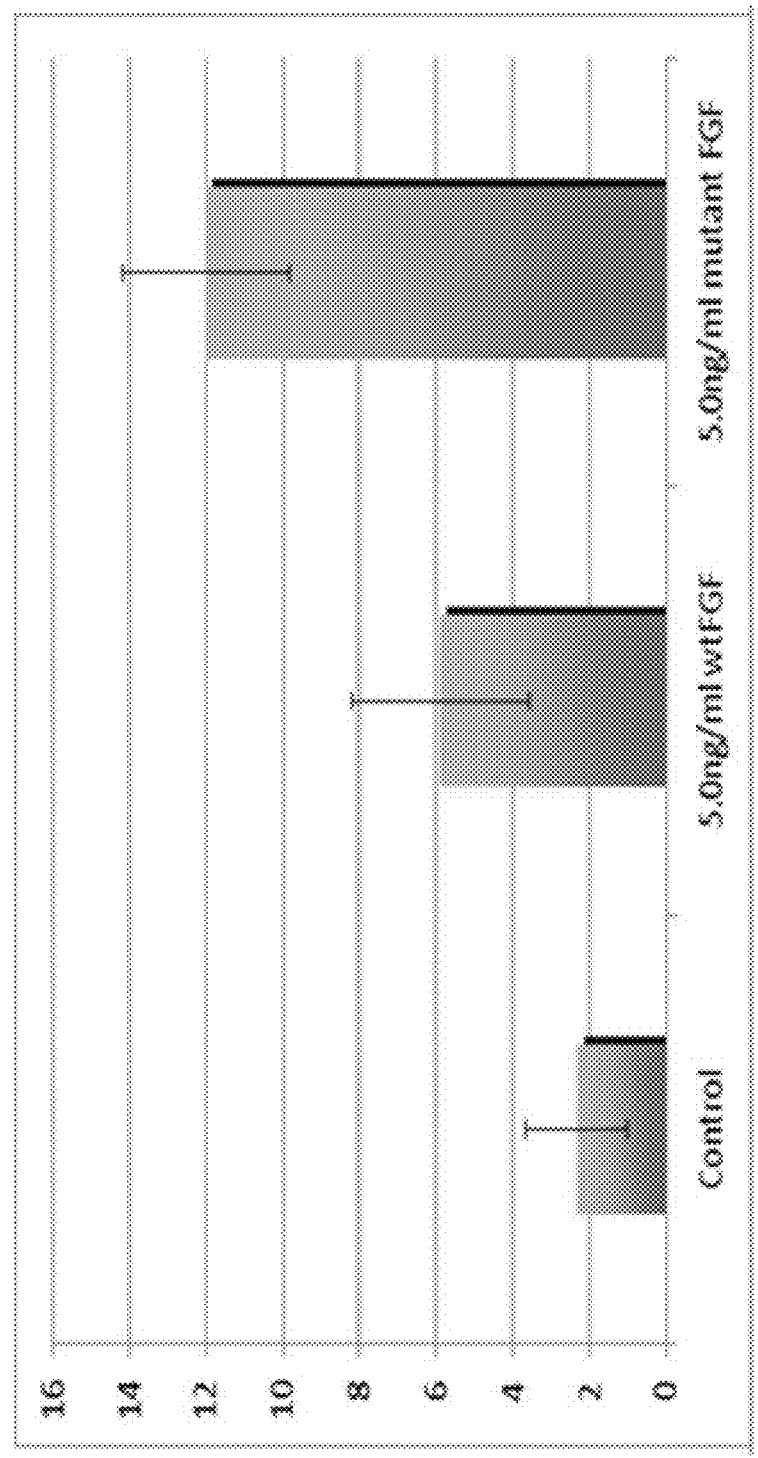

The wound healing potency of the wild-type FGF-1 was then compared to R136E. See FIG. 12. Results from this assay indicate that R136E has a pronounced (~two fold) effect compared to that of WT in inducing endothelial cell proliferation and migration to the site of wound at a much larger extent.

CONCLUSIONS

Heparin is proposed to function in two ways: it binds to FGFs and FGFRs, which is a requirement for the FGF/FGFR signaling complex formation, or it functions to stabilize the complex, thereby acting only to facilitate the formation of the FGF/FGFR complex. In 1991, Yayon et al. showed that Chinese hamster ovary cells expressing FGFR1, but lacking in the expression of cell-surface heparin-like glycosaminoglycans (HLGAGs), could not bind to FGF-2. However, upon addition of heparin or heparin sulfate, binding did occur. This led to the conclusion that heparin is a requirement for FGF/FGFR complex formation. However, the question remained unanswered as to whether the removal of heparin diminished binding because FGF or FGFR was destabilized, or because, without heparin, it is impossible for FGF and FGFR to come together to form the signaling complex. A more recent study involving the mutant K118E (K132E) of FGF-1 showed that this mutant had much lower activity than WT FGF-1. The study, however, went on to show that when this mutant was stabilized by additional mutations, mitogenic activity was restored. In the current study, several mutations were constructed in order to evaluate how stability versus heparin-binding affinity affects mitogenic activity of FGF-1. Despite each charge reversal mutation falling within the heparin-binding region of hFGF-1, the effects of each mutation on stability and heparin affinity differed greatly. Although arginine has been shown to bind heparin more tenaciously, the results of trypsin digestion, DSC, ITC and 2D $^1$H-$^{15}$N HSQC NMR indicate that the loss in heparin binding for R136E is less significant than that of WT. Based on all the above listed biophysical, biochemical and cell based activity assays, we found that R136E mutant of FGF1 exhibited an increased thermal, protease stability with an enhanced bioactivity.

SEQUENCE LISTING

```

```
                  115                 120                 125
Ala Ile Leu Phe Leu Pro Leu Pro Val Ser Ser Asp
    130                 135                 140

<210> SEQ ID NO 3
<211> LENGTH: 426
<212> TYPE: DNA
<213> ORGANISM: Homo sapiens
<220> FEATURE:
<221> NAME/KEY: misc_feature
<222> LOCATION: (1)..(426)
<223> OTHER INFORMATION: Nucleic Acid Sequence of FGF-1R136E

<400> SEQUENCE: 3
atgtttaatc tgcctccagg gaattacaag aagcccaaac tcctctactg tagcaacggg      60
ggccacttcc tgaggatcct tccggatggc acagtggatg ggacaaggga caggagcgac     120
cagcacattc agctgcagct cagtgcggaa agcgtggggg aggtgtatat aaagagtacc     180
gagactggcc agtacttggc catggacacc gacgggcttt tatacggctc acagacacca     240
aatgaggaat gtttgttcct ggaaaggctg gaggagaacc attacaacac ctatatatcc     300
aagaagcatg cagagaagaa ttggtttgtt ggcctcaaga agaatgggag ctgcaaacgc     360
ggtcctgaga ctcactatgg ccagaaagca atcttgtttc tccccctgcc agtctcttct     420
gattaa                                                                426

<210> SEQ ID NO 4
<211> LENGTH: 140
<212> TYPE: PRT
<213> ORGANISM: Homo sapiens
<220> FEATURE:
<221> NAME/KEY: misc_feature
<222> LOCATION: (1)..(140)
<223> OTHER INFORMATION: Amino acid sequence of FGF-1R136E (140)

<400> SEQUENCE: 4

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Glu Thr His Tyr Gly Gln Lys
        115                 120                 125

Ala Ile Leu Phe Leu Pro Leu Pro Val Ser Ser Asp
    130                 135                 140

<210> SEQ ID NO 5
<211> LENGTH: 426
<212> TYPE: DNA
<213> ORGANISM: Homo sapiens
<220> FEATURE:
<221> NAME/KEY: misc_feature
```

<222> LOCATION: (1)..(426)
<223> OTHER INFORMATION: Nucleic Acid Sequence of FGF-1R136D

<400> SEQUENCE: 5

```
atgtttaatc tgcctccagg gaattacaag aagcccaaac tcctctactg tagcaacggg      60
ggccacttcc tgaggatcct tccggatggc acagtggatg ggacaaggga caggagcgac     120
cagcacattc agctgcagct cagtgcggaa agcgtggggg aggtgtatat aaagagtacc     180
gagactggcc agtacttggc catggacacc gacgggcttt tatacggctc acagacacca     240
aatgaggaat gtttgttcct ggaaaggctg gaggagaacc attacaacac ctatatatcc     300
aagaagcatg cagagaagaa ttggtttgtt ggcctcaaga agaatgggag ctgcaaacgc     360
ggtcctgata ctcactatgg ccagaaagca atcttgtttc tccccctgcc agtctcttct     420
gattaa                                                                426
```

<210> SEQ ID NO 6
<211> LENGTH: 140
<212> TYPE: PRT
<213> ORGANISM: Homo sapiens
<220> FEATURE:
<221> NAME/KEY: misc_feature
<222> LOCATION: (1)..(140)
<223> OTHER INFORMATION: Amino acid sequence of FGF-1R136D

<400> SEQUENCE: 6

```
Phe Asn Leu Pro Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Asp Thr His Tyr Gly Gln Lys
        115                 120                 125

Ala Ile Leu Phe Leu Pro Leu Pro Val Ser Ser Asp
    130                 135                 140
```

<210> SEQ ID NO 7
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: Nucleic Acid Sequence of wtFGF-2

<400> SEQUENCE: 7

```
atggcagccg ggagcatcac cacgctgccc gccttgcccg aggatggcgg cagcggcgcc      60
ttcccgcccg ccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
```

```
cgttacctgg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctag                 468
```

<210> SEQ ID NO 8
<211> LENGTH: 155
<212> TYPE: PRT
<213> ORGANISM: Homo sapiens
<220> FEATURE:
<221> NAME/KEY: misc_feature
<222> LOCATION: (1)..(155)
<223> OTHER INFORMATION: Amino acid sequence of wtFGF-2 with the K138 site

<400> SEQUENCE: 8

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 9
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: Nucleic Acid Sequence of FGF-2K138E

<400> SEQUENCE: 9

```
atggcagccg ggagcatcac cacgctgccc gccttgcccg aggatggcgg cagcggcgcc    60
ttcccgcccg gccacttcaa ggaccccaag cggctgtact gcaaaaacgg ggcttcttc     120 ctgcgcatcc accccgacgg ccgagttgac ggggtccggg agaagagcga ccctcacatc    180
aagctacaac ttcaagcaga agagagagga gttgtgtcta tcaaaggagt gtgtgctaac    240
cgttacctgg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc cgaaacagga    420
cctgggcaga aagctatact ttttcttcca atgtctgcta agagctag                 468
```

<210> SEQ ID NO 10
<211> LENGTH: 155
<212> TYPE: PRT
<213> ORGANISM: Homo sapiens
<220> FEATURE:
<221> NAME/KEY: misc_feature
<222> LOCATION: (1)..(155)
<223> OTHER INFORMATION: Amino acid sequence of FGF-2K138E

<400> SEQUENCE: 10

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Glu Thr Gly Pro Gly Gln Lys
    130                 135                 140

Ala Ile Leu Phe Leu Pro Met Ser Ala Lys Ser
145                 150                 155
```

<210> SEQ ID NO 11
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: Nucleic Acid Sequence of FGF-2K138D

<400> SEQUENCE: 11

```
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc cgacacagga     420
cctgggcaga aagctatact ttttcttcca atgtctgcta agagctag                  468
```

<210> SEQ ID NO 12
<211> LENGTH: 155
<212> TYPE: PRT
<213> ORGANISM: Homo sapiens
<220> FEATURE:
<221> NAME/KEY: misc_feature
<222> LOCATION: (1)..(155)

```
<223> OTHER INFORMATION: Amino acid sequence of FGF-2K138D

<400> SEQUENCE: 12

Met Ala Ala Gly Ser Ile Thr Thr Leu Pro Ala Leu Pro Glu Asp Gly
1               5                   10                  15
Gly Ser Gly Ala Phe Pro Pro Gly His Phe Lys Asp Pro Lys Arg Leu
            20                  25                  30
Tyr Cys Lys Asn Gly Gly Phe Phe Leu Arg Ile His Pro Asp Gly Arg
        35                  40                  45
Val Asp Gly Val Arg Glu Lys Ser Asp Pro His Ile Lys Leu Gln Leu
    50                  55                  60
Gln Ala Glu Glu Arg Gly Val Val Ser Ile Lys Gly Val Cys Ala Asn
65                  70                  75                  80
Arg Tyr Leu Ala Met Lys Glu Asp Gly Arg Leu Leu Ala Ser Lys Cys
                85                  90                  95
Val Thr Asp Glu Cys Phe Phe Phe Glu Arg Leu Glu Ser Asn Asn Tyr
            100                 105                 110
Asn Thr Tyr Arg Ser Arg Lys Tyr Thr Ser Trp Tyr Val Ala Leu Lys
        115                 120                 125
Arg Thr Gly Gln Tyr Lys Leu Gly Ser Asp Thr Gly Pro Gly Gln Lys
    130                 135                 140
Ala Ile Leu Phe Leu Pro Met Ser Ala Lys Ser
145                 150                 155

<210> SEQ ID NO 13
<211> LENGTH: 33
<212> TYPE: DNA
<213> ORGANISM: Artificial Sequence
<220> FEATURE:
<223> OTHER INFORMATION: Synthetic primer: wtFGF

<400> SEQUENCE: 13
tgcaaacgcg gtcctcggac tcactatggc cag                                33

<210> SEQ ID NO 14
<211> LENGTH: 33
<212> TYPE: DNA
<213> ORGANISM: Artificial Sequence
<220> FEATURE:
<223> OTHER INFORMATION: Synthetic primer: R136E

<400> SEQUENCE: 14
tgcaaacgcg gtcctgagac tcactatggc cag                                33

<210> SEQ ID NO 15
<211> LENGTH: 33
<212> TYPE: DNA
<213> ORGANISM: Artificial Sequence
<220> FEATURE:
<223> OTHER INFORMATION: Synthetic primer: R136K

<400> SEQUENCE: 15
tgcaaacgcg gtcctaagac tcactatggc cag                                33
```

We claim:

1. A FGF polypeptide comprising a polypeptide selected from the group consisting of SEQ ID NO: 4, SEQ ID NO: 6, SEQ ID NO: 10, SEQ ID NO: 12, and a polypeptide having 80% sequence identity to SEQ ID NOs: 4, 6, 10 or 12 and comprising amino acid residue of 122 of SEQ ID NO: 4 or SEQ ID NO: 6 or amino acid residue 138 of SEQ ID NO: 10 or SEQ ID NO: 12.

2. The FGF polypeptide of claim 1, wherein the FGF polypeptide comprises SEQ ID NO: 4 or a polypeptide having 80% sequence identity to SEQ ID NO: 4 and comprising amino acid residue of 122 of SEQ ID NO: 4.

3. The FGF polypeptide of claim 2, wherein the FGF polypeptide comprises SEQ ID NO: 4.

4. A fusion protein comprising the FGF polypeptide of claim 1 and a membrane permeable peptide.

5. A pharmaceutical composition comprising the FGF polypeptide of claim 1 and a pharmaceutical carrier.

6. A hydrogel comprising the FGF polypeptide of claim 1.

7. A method of treating a wound comprising administering the FGF polypeptide of claim 1 to a subject in an amount effective to heal the wound.

8. The method of claim 7, wherein the subject is a human.

9. The FGF polypeptide of claim 1, wherein the FGF polypeptide comprises SEQ ID NO: 6 or a polypeptide having 80% sequence identity to SEQ ID NO: 6 and comprising amino acid residue of 122 of SEQ ID NO: 6.

10. The FGF polypeptide of claim 9, wherein the FGF polypeptide comprises SEQ ID NO: 6.

11. A pharmaceutical composition comprising the FGF polypeptide of claim 9 and a pharmaceutical carrier.

12. A hydrogel comprising the FGF polypeptide of claim 9.

13. The FGF polypeptide of claim 1, wherein the FGF polypeptide comprises SEQ ID NO: 10 or a polypeptide having 80% sequence identity to SEQ ID NO: 10 and comprising amino acid residue of 138 of SEQ ID NO: 10.

14. The FGF polypeptide of claim 13, wherein the FGF polypeptide comprises SEQ ID NO: 10.

15. A pharmaceutical composition comprising the FGF polypeptide of claim 13 and a pharmaceutical carrier.

16. A hydrogel comprising the FGF polypeptide of claim 13.

17. The FGF polypeptide of claim 1, wherein the FGF polypeptide comprises SEQ ID NO: 12 or a polypeptide having 80% sequence identity to SEQ ID NO: 12 and comprising amino acid residue of 138 of SEQ ID NO: 12.

18. The FGF polypeptide of claim 17, wherein the FGF polypeptide comprises SEQ ID NO: 12.

19. A pharmaceutical composition comprising the FGF polypeptide of claim 17 and a pharmaceutical carrier.

20. A hydrogel comprising the FGF polypeptide of claim 17.

* * * * *